US 6,699,722 B2

(12) United States Patent
Bauer et al.

(10) Patent No.: US 6,699,722 B2
(45) Date of Patent: Mar. 2, 2004

(54) POSITIVE DETECTION LATERAL-FLOW APPARATUS AND METHOD FOR SMALL AND LARGE ANALYTES

(75) Inventors: Jeffrey S. Bauer, San Diego, CA (US); Timothy P. Hyatt, Dundee, OR (US); Huiying Wang, Portland, OR (US)

(73) Assignee: A-Fem Medical Corporation, Wilsonville, OR (US)

( * ) Notice: Subject to any disclaimer, the term of this patent is extended or adjusted under 35 U.S.C. 154(b) by 0 days.

(21) Appl. No.: 09/835,304

(22) Filed: Apr. 13, 2001

(65) Prior Publication Data

US 2002/0142291 A1 Oct. 3, 2002

Related U.S. Application Data

(60) Provisional application No. 60/203,696, filed on May 11, 2000, and provisional application No. 60/197,365, filed on Apr. 14, 2000.

(51) Int. Cl.[7] ............................................. G01N 33/543
(52) U.S. Cl. .................... 436/518; 435/7.1; 435/7.92; 436/514; 436/541; 422/56; 422/57
(58) Field of Search ..................... 435/5, 7.1, 7.42, 435/810, 287.1; 436/514, 518, 541, 808, 109; 422/56, 58, 61, 57

(56) References Cited

U.S. PATENT DOCUMENTS

| 3,464,560 A | 9/1969 | Clement et al. |
| 3,600,306 A | 8/1971 | Tocci |
| 3,667,607 A | 6/1972 | Brandt |
| 3,697,639 A | 10/1972 | McCuller |
| 3,902,847 A | 9/1975 | Busch et al. |
| 4,168,146 A | 9/1979 | Grubb et al. |
| 4,235,601 A | 11/1980 | Deutsch et al. |
| 4,258,001 A | 3/1981 | Pierce et al. |
| 4,275,149 A | 6/1981 | Litman et al. |
| 4,313,734 A | 2/1982 | Leuvering |
| 4,366,241 A | 12/1982 | Tom et al. |
| 4,373,932 A | 2/1983 | Gribnau et al. |

(List continued on next page.)

FOREIGN PATENT DOCUMENTS

| DE | 3043608 | 5/1982 |
| EP | 0125118 | 11/1984 |
| EP | 0 296 724 B1 | 1/1985 |

(List continued on next page.)

*Primary Examiner*—Long V. Le
*Assistant Examiner*—Gary W. Counts
(74) *Attorney, Agent, or Firm*—Klarquist Sparkman, LLP

(57) ABSTRACT

Methods and devices for the detection and/or quantification of an analyte in a sample are provided. These are positive detection methods and devices, in that the more analyte is present in the sample, the stronger the signal that is provided. Devices of the invention include a mobilization zone including a mobile or mobilizable detectable analyte analog, a sample application area, primary and secondary capture areas each including an immobilized binding partner having a binding affinity for the analyte being tested for a detectable analyte analog. The mobilization zone, sample application area, primary and secondary capture area are in fluid continuous contact with each other. In these devices, the first immobilized binding partner has an equal or lower apparent affinity for the analyte than it has for the detectable analyte analog. Methods of this invention involve introducing a sample (which is suspected of containing the analyte to be tested for) to a device such as those described herein, and permitting the sample to migrate from the application area to and through the first and secondary binding zones. A detectable tracer conjugate is also permitted to migrate through the device, usually slightly behind the sample so that any analyte in the sample contacts the first binding partner before the conjugate. Results of such methods are read based on the presence and/or intensity of the detectable signal given by conjugate that binds in the second capture area.

39 Claims, 6 Drawing Sheets

U.S. PATENT DOCUMENTS

| | | |
|---|---|---|
| 4,425,438 A | 1/1984 | Bauman et al. |
| 4,434,236 A | 2/1984 | Freytag |
| 4,442,204 A | 4/1984 | Greenquist et al. |
| 4,446,232 A | 5/1984 | Liotta |
| 4,632,901 A | 12/1986 | Valkirs et al. |
| 4,703,017 A | 10/1987 | Campbell et al. |
| 4,743,560 A | 5/1988 | Campbell et al. |
| 4,770,853 A | 9/1988 | Bernstein |
| 4,366,241 A | 10/1988 | Tom et al. |
| 4,775,636 A | 10/1988 | Moeremans et al. |
| 4,803,170 A | 2/1989 | Stanton et al. |
| 4,806,311 A | 2/1989 | Greenquist |
| 4,806,312 A | 2/1989 | Greenquist |
| 4,824,870 A | 4/1989 | Pemawansa et al. |
| 4,851,356 A | 7/1989 | Canfield et al. |
| 4,853,335 A | 8/1989 | Olsen et al. |
| 4,855,240 A | 8/1989 | Rosenstein et al. |
| 4,857,453 A | 8/1989 | Ullman et al. |
| 4,861,711 A | 8/1989 | Friesen et al. |
| 4,868,108 A | 9/1989 | Bahar et al. |
| 4,916,056 A | 4/1990 | Brown, III et al. |
| 4,943,522 A | 7/1990 | Eisenger et al. |
| 4,945,042 A | 7/1990 | Geiger et al. |
| 4,954,452 A | 9/1990 | Yost et al. |
| 4,956,275 A | 9/1990 | Zuk et al. |
| 4,959,305 A | 9/1990 | Woodrum |
| 4,963,468 A | 10/1990 | Olson |
| 4,981,786 A | 1/1991 | Dafforn et al. |
| 4,999,285 A | 3/1991 | Stiso |
| 5,008,080 A | 4/1991 | Brown, III et al. |
| 5,073,484 A | 12/1991 | Swanson et al. |
| 5,075,078 A | 12/1991 | Osikowicz et al. |
| 5,089,391 A | 2/1992 | Buechler et al. |
| 5,096,837 A | 3/1992 | Fan et al. |
| 5,102,788 A | 4/1992 | Cole |
| 5,114,673 A | 5/1992 | Berger et al. |
| 5,120,643 A | 6/1992 | Ching et al. |
| 5,126,241 A | 6/1992 | Schenk |
| 5,141,850 A | 8/1992 | Cole et al. |
| 5,145,789 A | 9/1992 | Corti et al. |
| 5,160,626 A | 11/1992 | Pemawansa et al. |
| 5,182,216 A | 1/1993 | Clayton et al. |
| 5,229,073 A | 7/1993 | Luo et al. |
| 5,238,652 A | 8/1993 | Sun et al. |
| 5,244,815 A | 9/1993 | Guirguis |
| 5,266,497 A | 11/1993 | Imai et al. |
| 5,354,692 A | 10/1994 | Yang et al. |
| 5,356,782 A | 10/1994 | Moorman et al. |
| 5,416,000 A | 5/1995 | Allen et al. |
| 5,420,016 A * | 5/1995 | Boguslaski et al. ............ 435/12 |
| 5,424,193 A | 6/1995 | Pronovost et al. |
| 5,451,504 A | 9/1995 | Fitzpatrick et al. |
| 5,451,507 A | 9/1995 | Skold et al. |
| 5,458,852 A | 10/1995 | Buechler |
| 5,470,713 A | 11/1995 | El Shami et al. |
| 5,489,537 A | 2/1996 | Van Aken |
| 5,527,686 A | 6/1996 | Fitzpatrick et al. |
| 5,569,608 A | 10/1996 | Sommer |
| 5,580,794 A | 12/1996 | Allen |
| 5,591,645 A | 1/1997 | Rosenstein |
| 5,602,040 A | 2/1997 | May et al. |
| 5,622,871 A | 4/1997 | May et al. |
| 5,654,162 A | 8/1997 | Guire et al. |
| 5,656,502 A | 8/1997 | MacKay et al. |
| 5,656,503 A | 8/1997 | May et al. |
| 5,710,009 A | 1/1998 | Fitzpatrick et al. |
| 5,712,172 A | 1/1998 | Huang et al. |
| 5,770,460 A | 6/1998 | Pawlak et al. |
| 5,798,273 A | 8/1998 | Shuler et al. |
| 5,871,905 A | 2/1999 | Thieme et al. |
| 5,877,028 A | 3/1999 | Chandler et al. |
| 5,989,925 A | 11/1999 | Fitzpatrick et al. |
| 6,001,658 A | 12/1999 | Fredrickson |
| 6,027,943 A | 2/2000 | Kang et al. |
| 6,030,770 A | 2/2000 | Brust |
| 6,033,918 A | 3/2000 | Hatch et al. |
| 6,037,455 A | 3/2000 | Buechler |
| 6,352,862 B1 * | 3/2002 | Davis et al. ................. 436/510 |
| 2001/0044118 A1 * | 11/2001 | Ghoshal et al. .............. 435/7.1 |

FOREIGN PATENT DOCUMENTS

| | | |
|---|---|---|
| EP | 0280559 | 8/1988 |
| EP | 0281327 | 9/1988 |
| EP | 0282192 | 9/1988 |
| EP | 0299428 | 1/1989 |
| EP | 0 362 809 B1 | 1/1994 |
| GB | 1 440 464 | 6/1976 |
| WO | WO8808534 | 11/1988 |
| WO | WO 89/05978 | 6/1989 |
| WO | WO9212428 | 7/1992 |
| WO | WO9112528 | 8/1992 |
| WO | WO 93/03175 | 2/1993 |
| WO | WO9401775 | 1/1994 |
| WO | WO 94/16329 | 7/1994 |
| WO | WO 97/06439 | 2/1997 |
| WO | WO 98/23958 | 6/1998 |
| WO | WO 98/36278 | 8/1998 |
| WO | WO 98/39657 | 9/1998 |
| WO | WO 99/50656 | 10/1999 |

OTHER PUBLICATIONS

Lou et al., "One–Step Competitive Immunochromatographic Assay for Semiquantitative Determination of Lipoprotein(a) in Plasma," *Clin. Chem.* 39/4:619–624 (1993).

Hansel et al., "Single–Reagent Polarisation Fluoroimmunoassay for Cotinine (a Nicotine Metabolite) in Urine," *Ann Clin Biochem* 23:596–602 (1986).

"ImmunoDip," Diagnositc Chemicals Limited, 70025.If, 1 page (6/97).

* cited by examiner

Apply Sample

Allow strip to develop

| A | Analyte from sample | ↑ | Liquid flow |
|---|---|---|---|
| A'-L-🅣 | Analyte analog/Linker/Label Conjugate | | |
| αA⧸ | Primary capture antibody | | |
| αA₂⧸ | Secondary capture antibody | | |

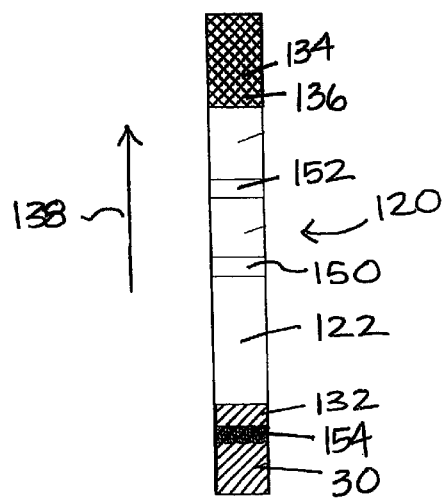
FIG 2A
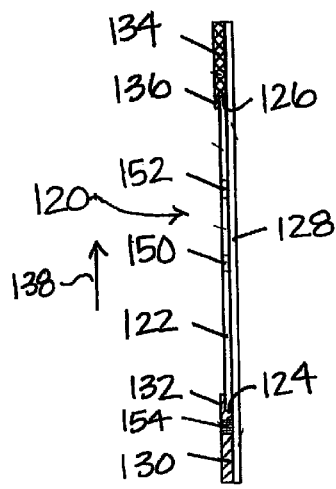
FIG 2B
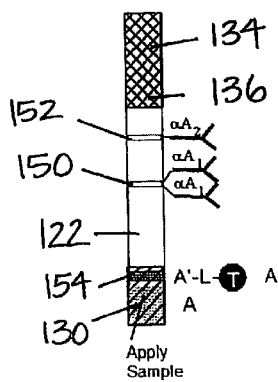
FIG 2C
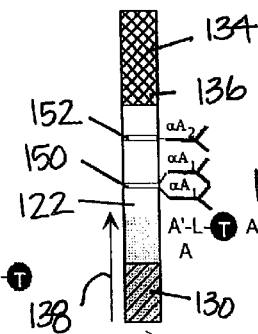
FIG 2D
FIG 2E
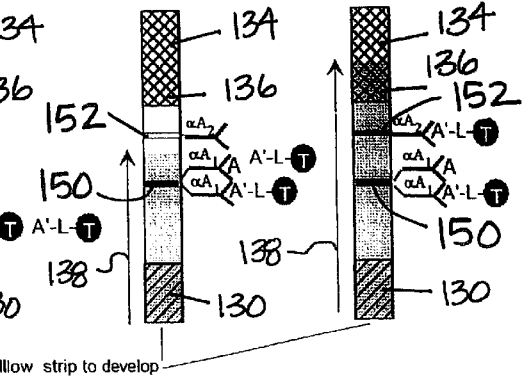
FIG 2F
| A | Analyte from sample |
| A'-L-🅣 | Analyte analog/Linker/Label Conjugate |
| αA₁ | Primary capture antibody |
| αA₂ | Secondary capture antibody |
Liquid flow

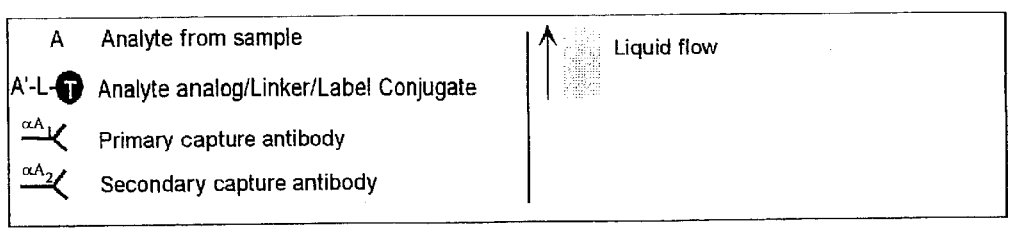

Cotinine Test Strips

Cotinine Concentration (ng/mL)

Cotinine Standard Curve

Cotinine Test Strips

Cotinine Concentration (ng/mL)

POSITIVE DETECTION LATERAL-FLOW APPARATUS AND METHOD FOR SMALL AND LARGE ANALYTES

This application claims priority from U.S. Provisional Application No. 60/197,365 filed Apr. 14, 2000, and U.S. Provisional Application No. 60/203,696 filed May 11, 2000, both of which are incorporated herein by reference.

FIELD

The present invention relates to sensitive lateral-flow methods and devices for determining the presence and/or amount of small and large analytes in fluid samples. The present invention provides a direct or positive detection result (i.e. increasing signal with increasing analyte concentration) in a sequential binding format.

BACKGROUND

Analytical tests have been developed for the routine identification or monitoring of physiological and pathological conditions (e.g., pregnancy, cancer, endocrine disorders, infectious diseases) using different biological samples (e.g., urine, serum, plasma, blood, saliva), and for analysis of environmental samples (e.g., natural fluids and industrial plant effluents) for instance for contamination. Many of these tests are based on the highly specific interactions between specific binding pairs. Examples of such binding pairs include antigen/antibody, hapten/antibody, lectin/carbohydrate, apoprotein/cofactor and biotin/(strept)avidin. Furthermore, many of these tests involve devices (e.g., solid phase, lateral-flow test strips, flowthrough tests) with one or more of the members of a binding pair attached to a mobile or immobile solid phase material such as latex beads, glass fibers, glass beads, cellulose strips or nitrocellulose membranes (U.S. Pat. Nos. 4,703,017; 4,743,560; 5,073,484).

Immunochromatographic assays fall into two principal categories: "sandwich" and "competitive." In general, sandwich immunochromatographic procedures call for mixing the sample that may contain the analyte to be assayed with antibodies to the analyte. These antibodies are mobile and typically are linked to a label or another signaling reagent, such as dyed latex, a colloidal metal sol, or a radioisotope. This mixture is then applied to a chromatographic medium containing a band or zone of immobilized antibodies to the analyte of interest. The chromatographic medium often is in the form of a strip that resembles a dipstick. When the complex of the molecule to be assayed and the labeled antibody reaches the zone of the immobilized antibodies on the chromatographic medium, binding occurs and the bound, labeled antibodies are localized at the zone. This indicates the presence of the molecule to be assayed. This technique can be used to obtain quantitative or semi-quantitative results. Examples of sandwich immunoassays performed on test strips are described in U.S. Pat. Nos. 4,168,146 and 4,366,241, each of which is incorporated herein by reference.

In competitive immunoassays, the label is typically a labeled analyte or analyte analogue that competes with any unlabeled analyte present in the sample for binding to an antibody. In such competitive assays, the analyte and labeled tracer molecule are simultaneously introduced to the binding agent such that these molecules compete for binding sites. Competitive immunoassays are typically used for detection of analytes such as haptens, each hapten being monovalent and capable of binding only one antibody molecule. Examples of competitive immunoassay devices are those disclosed by U.S. Pat. Nos. 4,235,601, 4,442,204 and 5,208,535, each of which is incorporated herein by reference.

Solid phase immunoassay devices, whether sandwich- or competition-type, provide sensitive detection of an analyte in a biological fluid sample. Solid phase immunoassay devices incorporate a solid support to which one member of a ligand-receptor pair, usually an antibody, antigen, or hapten, is bound. Common early forms of solid supports were plates, tubes, or beads of polystyrene, which were known from the fields of radioimmunoassay and enzyme immunoassay. More recently, a number of porous materials such as nylon, nitrocellulose, cellulose acetate, glass fibers, and other porous polymers have been employed as solid supports.

In the more common forms of dipstick assays, as typified by home pregnancy and ovulation detection kits, immunochemical components such as antibodies are bound to a solid phase. The assay device is "dipped" for incubation into a sample suspected of containing the subject analyte. Enzyme-labeled antibody is then added, either simultaneously or after an incubation period. The device next is washed and then inserted into a second solution containing a substrate for the enzyme. The enzyme-label, if present, interacts with the substrate, causing the formation of colored products, which either deposit as a precipitate onto the solid phase or produce a visible color change in the substrate solution. EP-A 0 125 118 discloses such a sandwich type dipstick immunoassay. EP-A 0 282 192 discloses a dipstick device for use in competition type assays.

Flow-through type immunoassay devices (such as test strips) were designed to obviate the need for incubation and washing steps associated with dipstick assays. U.S. Pat. No. 4,632,901 discloses a sandwich immunoassay device wherein antibody (specific to a target antigen analyte) is bound to a porous membrane or filter to which a liquid sample is added. As the liquid flows through the membrane, target analyte binds to the antibody. The addition of sample is followed by addition of labeled antibody. The visual detection of labeled antibody provides an indication of the presence of target antigen analyte in the sample.

Migration assay devices usually incorporate within them reagents that have been attached to colored labels, thereby permitting visible detection of the assay results without addition of further substances. See, for example, U.S. Pat. No. 4,770,853; WO 88/08534; and EP-A 0 299 428.

There are a number of commercially available lateral-flow type tests and patents disclosing methods for the detection of large analytes (MW greater than 1,000 Daltons). U.S. Pat. No. 5,229,073 describes a semiquantitative competitive immunoassay lateral flow method for measuring plasma lipoprotein levels. This method utilizes a plurality of capture zones or lines containing immobilized antibodies to bind both the labeled and free lipoprotein to give a semi-quantitative result.

U.S. Pat. No. 5,591,645 provides a chromatographic test strip with at least two portions. The first portion includes a movable tracer and the second portion includes an immobilized binder capable of binding to the analyte. Additional examples of lateral-flow tests for large analytes are disclosed in the following patent documents: U.S. Pat. Nos. 4,168,146; 4,366,241; 4,855,240; 4,861,711; 5,120,643; European Patent No. 0296724; WO 97/06439; and WO 98/36278.

There are also a limited number of lateral-flow type tests for the detection of small-analytes (MW 100–1,000 Daltons). Generally, these small analyte tests involve "typical" competitive inhibition to produce negative or indirect reporting results (i.e., reduction of signal with increasing analyte concentration), as exemplified by U.S. Pat. No. 4,703,017.

Several approaches have been developed for detecting small analytes using lateral-flow tests that produce positive or direct reporting results (i.e., increase in signal with increasing analyte concentration). These include, for instance, U.S. Pat. Nos. 5,451,504; 5,451,507; 5,798,273; and 6,001,658.

U.S. Pat. No. 5,451,504 provides a method with three specific zones (mobilization, trap and detection) each containing a different latex conjugate to yield a positive signal. The mobilization zone contains labeled antibody to bind the analyte in the sample. In the trap zone, unbound, labeled antibody is then trapped by immobilized analyte analog. The detection zone captures the labeled analyte-antibody complex. A disadvantage of this method is that the analyte-analog in the trap zone competes with the labeled analyte-antibody complex formed during migration and may cause false negative results.

U.S. Pat. No. 5,451,507 describes a two-zone, disconnected immunochromatographic method. The first zone has non-diffusively bound reagent that binds with a component, e.g., an analyte analog bound to, or capable of becoming bound to, a member of a signal producing system. The second zone binds to the component only when the analyte to be tested is present. The distance the component migrates into the second zone is directly related to the concentration of analyte.

U.S. Pat. No. 5,798,273 discloses a lateral flow device that includes a capture zone with immobilized analyte analog and one or more read-out zones to bind labeled analyte-analog. A disadvantage of this disclosed method is the requirement to premix sample, antibody and colored label prior to application to the sample addition area of the lateral flow device.

U.S. Pat. No. 6,001,658 discloses a test strip device with a diffusible, labeled binding partner that binds with analyte, an immobilized analyte, and a detection area containing an immobilized antibody.

A continuing need exists for a sensitive, rapid and single step method to detect and quantify both large and small analytes at low concentrations (such as ng/ml or less).

SUMMARY

The present invention provides sensitive, rapid devices (in the form of a test strip) for determining the presence and/or amount (at ng/ml levels) of small and/or large analytes in a fluid sample. The invention also provides methods for the determination of the presence and/or amount of one or more components (e.g., analytes) in a sample. Results from the methods and devices disclosed herein can be positively read directly from the assay device by visual inspection or using an electronic reader (such as a scanner).

The methods and devices disclosed herein can be used to detect analytes in various types of fluid, including biological specimens (such as blood, serum, plasma, urine, saliva, milk) and environmental samples (such as industrial plant effluent or natural fluids). Any known analyte with an appropriate analyte-specific antibody or other binding partner can be easily detected and/or quantified using the disclosed methods and devices. In certain examples of embodiments, a tracer is used, such as colored or otherwise detectable particles (e.g., colored latex or colloidal gold) conjugated to the analyte or an analyte-analog, which tracers are collectively referred to as the conjugate.

Devices of the invention include a mobilization zone, a sample application area, and primary and secondary capture areas. Each of the capture areas includes an immobilized binding partner (such as an antibody) having a binding affinity for the analyte being tested and for the detectable conjugate. A mobilization zone, sample application area, and primary and secondary capture areas are in fluid continuous contact with each other, e.g., on a lateral flow chromatography strip. In these devices, the first immobilized binding partner binds the analyte and detectable conjugate. However, to the extent that analyte is present in the sample, the labeled conjugate is less able or unable to bind in the primary capture zone and instead continues to migrate along the strip toward the secondary capture zone, where it binds with the secondary binding partner. The labeled conjugate therefore provides a positive signal, in proportion to the amount of analyte present in the sample, in the secondary capture zone.

In some embodiments, the specific binding agent in the primary capture zone may have a higher affinity for the analyte than the labeled conjugate, such that the conjugate is less preferentially bound in the primary capture zone and preferentially passes through to the secondary capture zone. However, the binding agent in the primary capture zone may have an equal affinity for the analyte, and the labeled analyte will still pass through the primary capture zone to bind in the secondary capture zone and emit a signal proportional to the presence of analyte in the sample. It is also possible that the binding agent in the primary capture zone may have a lower affinity for the analyte in some embodiments, and still provide a substantially quantitative signal from the secondary capture zone, with the signal proportional to the amount of analyte in the sample.

Other embodiments of the test strip permit sequential migration of the analyte and labeled analyte analog, such that the analyte migrates in advance of the labeled conjugate, to be bound by the specific binding agent in the primary capture zone. Since sites in the primary capture zone are already occupied when the labeled conjugate reaches the primary capture zone, the conjugate continues to migrate along the strip to the secondary capture zone. The labeled conjugate then provides a signal in the secondary capture zone, which signal is proportionate to the amount of analyte in the sample.

Certain methods of this invention involve introducing a liquid sample (which is suspected of containing the analyte to be tested for) on to the test strip, and permitting the sample to migrate along the test strip by capillary action from the application area to and through the first and secondary binding zones. The tracer conjugate may be present in the application zone, in the path of migration, or applied separately to the strip. The conjugate also migrates along the test strip, for example slightly behind the sample, so that any analyte in the sample contacts the first binding partner before the analyte-tracer conjugate. If the analyte is present in the sample, it will bind to the first binding partner, and occupy binding sites that are then not available to bind the labeled conjugate. Hence the conjugate will migrate along the strip to the secondary binding zone, where the presence and/or intensity of the detectable signal positively indicates an amount of analyte in the sample.

The foregoing and other features and advantages of the invention will become more apparent from the following detailed description of several embodiments, which proceeds with reference to the accompanying Figures.

BRIEF DESCRIPTION OF THE FIGURES

FIG. 2A is a top plan view of a second embodiment of the test strip.

FIG. 2B is a side view of the test strip shown in FIG. 2A.

FIGS. 2C–2F are schematic top views of the test strip of FIG. 2A, illustrating the progressive advancement of a liquid specimen through the strip.

DETAILED DESCRIPTION OF PARTICULAR EMBODIMENTS

I. Abbreviations and Definitions

A. Abbreviations

CDTA: trans-1,2-diaminocyclohexane-N,N,N',N'-tetraacetic acid

EDTA: ethylenediamine tetraacetate

EGTA: ethyleneglycol-bis(β-oxyethylenenitrilo)-tetraacetic acid

Ig: immunoglobulin

IGEPAL: IGEPAL GA-630 (octylphenoxy) polyethoxyethanol

GAM: Goat-anti-mouse antibody

MAb: monoclonal antibody

NTA: nitriloacetic acid

PVA: polyvinyl alcohol PVP: p0 polyvinylpyrrolidone

B. Definitions

Figure 1A:
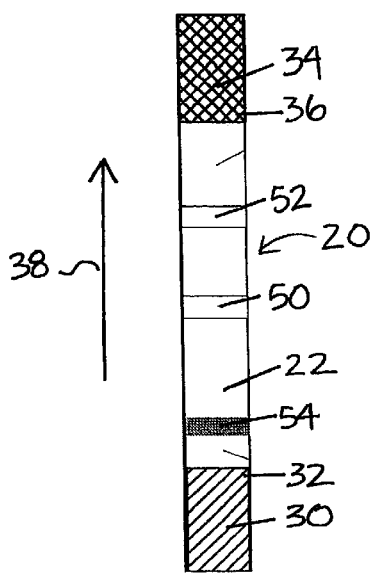
FIG. 1A is a top plan view of a first embodiment of the lateral flow test strip of the present invention.

Analyte—an atom, molecule, group of molecules or compound of natural or synthetic origin (e.g. drug, hormone, enzyme, growth factor antigen, antibody, hapten, lectin, apoprotein, cofactor) sought to be detected or measured that is capable of binding specifically to at least one binding partner (e.g. drug, hormone, antigen, antibody, hapten, lectin, apoprotein, cofactor).

The methods of this invention can be practiced with assays for virtually any analyte. The analytes may include, but are not limited to antibodies to infectious agents (such as HIV, HTLV, *Helicobacter pylori*, hepatitis, measles, mumps, or rubella), cocaine, benzoylecgonine, benzodizazpine, tetrahydrocannabinol, nicotine, ethanol theophylline, phenytoin, acetaminophen, lithium, diazepam, nortryptyline, secobarbital, phenobarbitol, methamphetamine, theophylline, testosterone, estradiol, estriol, 17-hydroxyprogesterone, progesterone, thyroxine, thyroid stimulating hormone, follicle stimulating hormone, luteinizing hormone, transforming growth factor alpha, epidermal growth factor, insulin-like growth factor I and II, growth hormone release inhibiting factor, IGA and sex hormone binding globulin; and other analytes including antibiotics (e.g., penicillin), glucose, cholesterol, caffeine, cotinine, corticosteroid binding globulin, PSA, or DHEA binding glycoprotein.

Analytes vary in size. Merely by way of example, small molecule analytes may be, for instance, <0.1 nm (such as cotinine or penicillin, each with a molecular weight of less than about 1,000 Daltons). However, analytes may be larger than this, including for instance immunoglobulin analytes (such as IgG, which is about 8 nm in length and about 160,000 Daltons).

Analyte analog—a modified analyte that has structural similarity to the unmodified analyte and can bind to at least one analyte binding partner. In certain embodiments of the invention, the analyte analog is an analyte-tracer conjugate, for instance a detectable analyte-tracer conjugate.

Antibody—a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

Antibodies may exist as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$——$C_H1$ by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially an Fab with part of the hinge region (see, *Fundamental Immunology*, W. E. Paul, ed., Raven Press, N.Y., 1993). While various antibody fragments are defined in terms of the digestion of an intact antibody, it will be appreciated that Fab' fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

Antibodies for use in the methods and devices of the invention can be monoclonal or polyclonal, but often will be monoclonal. Merely by way of example, such monoclonal antibodies can be prepared from murine hybridomas according to the classical method of Kohler and Milstein (Nature 256:495–497, 1975) or derivative methods thereof. Briefly, a mouse is repetitively inoculated with a few micrograms of the selected analyte compound (or a fragment thereof) over a period of a few weeks. In some instances, it will be beneficial to use an adjuvant or a carrier molecule to increase the immunogenicity and/or stability of the analyte in the animal system. The mouse is then sacrificed, and the antibody-producing cells of the spleen isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Meth. Enzymol.* 70:419–439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

Monoclonal antibodies to different analytes are commercially available. For instance, a monoclonal antibody to estriol-3 is produced by Fitzgerald Industries International (Concord, Mass.; Cat. #10-E37, Clone #M612039); likewise, Omega Biological, Inc. (Bozeman, Mont.) produces a monoclonal antibody to methamphetamine (Cat. #100-11-183, Clone Met 2).

Antigenic—a chemical or biochemical structure, determinant, antigen or portion thereof that is capable of inducing the formation of an antibody.

Binding affinity—a term that refers to the strength of binding of one molecule to another at a site on the molecule. If a particular molecule will bind to or specifically associate with another particular molecule, these two molecules are said to exhibit binding affinity for each other. Binding affinity is related to the association constant and dissociation constant for a pair of molecules, but it is not critical to the invention that these constants be measured or determined. Rather, affinities as used herein to describe interactions between molecules of the described methods and devices are generally apparent affinities (unless otherwise specified) observed in empirical studies, which can be used to compare the relative strength with which one molecule (e.g., an antibody or other specific binding partner) will bind two other molecules (e.g., an analyte and an analyte-tracer conjugate). The concepts of binding affinity, association constant, and dissociation constant are well known.

In the devices and methods of this invention, the immobilized specific binding partners do not generally have a lower binding affinity for the analyte-tracer conjugate than they do for the analyte being tested for in a sample. Rather, the immobilized binding partners will have the same apparent affinity for the analyte and analyte-tracer conjugate, or in some instances will have greater affinity for the analyte-tracer conjugate. In certain embodiments, an immobilized binding partner may have little or no affinity for the analyte while having strong or very strong affinity for the analyte tracer conjugate (for instance, this will be the case for some immobilized binding partners that are immobilized in the secondary capture zone).

Binding domain—the molecular structure associated with that portion of a receptor that binds ligand. More particularly, the binding domain may refer to a polypeptide, natural or synthetic, or nucleic acid encoding such a polypeptide, the amino acid sequence of which represents a specific (binding domain) region of a protein, which either alone or in combination with other domains, exhibits binding characteristics that are the same or similar to those of a desired ligand/receptor binding pair. Neither the specific sequences nor the specific boundaries of such domains are critical, so long as binding activity is exhibited. Likewise, used in this context, binding characteristics necessarily includes a range of affinities, avidities and specificities, and combinations thereof, so long as binding activity is exhibited.

Binding partner—any molecule or composition capable of recognizing and binding to a specific structural aspect of another molecule or composition. Examples of such binding partners and corresponding molecule or composition include antigen/antibody, hapten/antibody, lectin/carbohydrate, apoprotein/cofactor and biotin/(strept)avidin.

Chelator—(chelating resin) a composition that binds divalent cations. The binding can be reversible or irreversible. Binding of divalent cations generally renders them substantially unable to participate in chemical reactions with other moieties with which they come in contact. Chelators are well known and include ethylenediamine tetraacetate (EDTA), sodium citrate, ethyleneglycol-bis(β-oxyethylenenitrilo)-tetraacetic acid (EGTA), trans-1,2-diaminocyclohexaneN,N,N',N'-tetraacetic acid (CDTA), nitriloacetic acid (NTA), resins that contain moieties that bind divalent cations and the like. Chelators that remain in solid phase in the solution in question are referred to as chelating resins. Chelating resins can be used to pull the subject ion (e.g., $Ca^{2+}$) out of solution. Chelating resins include, but are not limited to, chelex resins containing iminodiacetate ions, resins containing free base polyamines, aminophosphonic acid, and the like.

Immunogen—a chemical or biochemical structure, determinant, antigen or portion thereof, that elicits an immune response, including, for example, polylysine, bovine serum albumin and keyhole limpet hemocyanin (KLH).

Label—any molecule or composition bound to an analyte, analyte, analog or binding partner that is detectable by spectroscopic, photochemical, biochemical, immunochemical, electrical, optical or chemical means. Examples of labels, including enzymes, colloidal gold particles, colored latex particles, have been disclosed (U.S. Pat. Nos. 4,275,149; 4,313,734; 4,373,932; and 4,954,452, each incorporated by reference herein).

The attachment of a compound (e.g., an analyte) to a label can be through covalent bonds, adsorption processes, hydrophobic and/or electrostatic bonds, as in chelates and the like, or combinations of these bonds and interactions and/or may involve a linking group.

Lateral flow device: Devices that include bibulous or non-bibulous matrices capable of transporting analytes and reagents to a pre-selected site. Many such devices are known, in which the strips are made of nitrocellulose, paper, cellulose, and other bibulous materials. Non-bibulous materials can be used, and rendered bibulous by applying a surfactant to the material.

Lateral flow chromatography strip: A test strip used in lateral flow chromatography, in which a test sample fluid, suspected of containing an analyte, flows (for example by capillary action) through the strip (which is frequently made of materials such as paper or nitrocellulose). The test fluid and any suspended analyte can flow along the strip to a detection zone in which the analyte (if present) interacts with a detection agent to indicate a presence, absence and/or quantity of the analyte.

Linking group—a chemical arm between two compounds, for instance a compound and a label (e.g., an analyte and a label). To accomplish the requisite chemical structure, each of the reactants must contain a reactive group. Representative combinations of such groups are amino with carboxyl to form amide linkages; carboxy with hydroxy to form ester linkages or amino with alkyl halides to form alkylamino linkages; thiols with thiols to form disulfides; or thiols with maleimides or alkylhalides to form thioethers. Hydroxyl, carboxyl, amino and other functionalities, where not present in the native compound may be introduced by known methods.

Likewise, a wide variety of linking groups may be employed. The structure of the linkage should be a stable covalent linkage formed to attach two compounds to each other (e.g., the label to the analyte). In some cases the linking group may be designed to be either hydrophilic or hydrophobic in order to enhance the desired binding characteristics, for instance of the modified ligand and its cognate receptor. The covalent linkages should be stable relative to the solution conditions to which linked compounds are subjected. Examples of linking groups will be from 1–20 carbons and 0–10 heteroatoms (NH, O, S) and may be branched or straight chain. Without limiting the foregoing, it should be obvious that only combinations of atoms that are chemically compatible comprise the linking group. For example, amide, ester, thioether, thiol ester, keto, hydroxyl, carboxyl, ether groups in combinations with carbon—carbon bonds are particular examples of chemically compatible linking groups.

Operable or contiguous contact—two solid components are in operable contact when they are in contact, either directly or indirectly, in such a manner that an aqueous liquid can flow from one of the two components to the other substantially uninterruptedly, by capillarity or otherwise. Direct or contiguous contact means that the two elements are in physical contact, such as edge-to-edge or front-to-back. When two components are in direct contact, they may overlap with an overlap of about 0.5 to about 3 mm. However, the components can be placed with abutting edges. "Indirect contact" means that the two elements are not in physical contact, but are bridged by one or more conductors. Operable contact can also be referred to as "fluid transmitting" or "fluid continuous" contact.

Positive/direct reporting—an increase in the reporting or detection signal with increasing analyte concentration.

Preservative—a substance showing antimicrobial properties, in particular bactericidal properties and, in some instances also antifungal properties.

Specific binding partner—a member of a pair of molecules that interact by means of specific, noncovalent interactions that depend on the three-dimensional structures of the molecules involved. Typical pairs of specific binding partners include antigen/antibody, hapten/antibody, hormone/receptor, nucleic acid strand/complementary nucleic acid strand, substrate/enzyme, inhibitor/enzyme, carbohydrate/lectin, biotin/(strept)avidin, and virus/cellular receptor.

The phrase "specifically binds to an analyte" or "specifically immunoreactive with," when referring to an antibody, refers to a binding reaction which is determinative of the presence of the analyte in the presence of a heterogeneous population of molecules such as proteins and other biologic molecules. Thus, under designated immunoassay conditions, the specified antibodies bind to a particular analyte and do not bind in a significant amount to other analytes present in the sample. A variety of immunoassay formats may be used to select antibodies specifically immunoreactive with a particular analyte. For example, solid-phase ELISA immunoassays are routinely used to select monoclonal antibodies specifically immunoreactive with a protein. See Harlow and Lane, *Antibodies, A Laboratory Manual*, CSHP, New York (1988), for a description of immunoassay formats and conditions that can be used to determine specific immunoreactivity.

II. Detailed Description of the Figures

FIGS. 1–3 show three different embodiments of a lateral flow chromatography strip of the present invention, which will be individually described.

Embodiment of FIG. 1

Figure 1B:
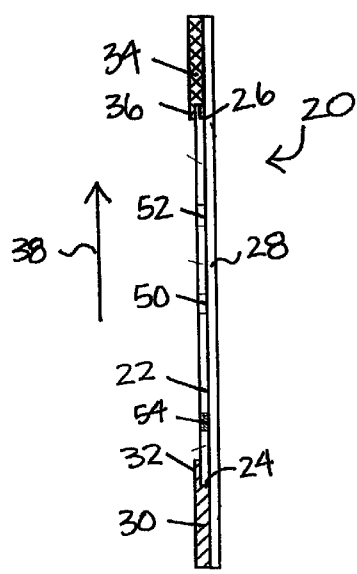
FIG. 1B is a side view of the test strip shown in FIG. 1A.
Figure 1C:
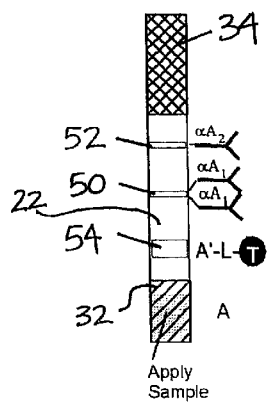
FIGS. 1C–1F are schematic top views of the test strip of FIG. 1A, illustrating the progressive advancement of a liquid specimen by capillary action through the strip.

The lateral flow chromatography strip 20 is seen in isolation in FIGS. 1A and 1B, which show strip 20 to include an elongated, narrow, bibulous liquid collection member 22 with a flat proximal edge 24 and a flat distal edge 26. Strip 20 is mounted on a rigid or semi-rigid plastic support 28, and a proximal absorbent sample collection pad 30 is also mounted to the support 28 such that it is contiguous with collection member 22, and includes a reduced thickness extension 32 that extends in a distal direction over member 22. A distal reservoir pad 34 is attached to a distal end of support 28, and reservoir pad 34 includes a reduced thickness extension 36 that overlaps subjacent collection member 22. Liquid placed on collection pad 30 moves by capillary action in a distal direction 38 through collection member 22 into reservoir pad 34.

Figure 1D:
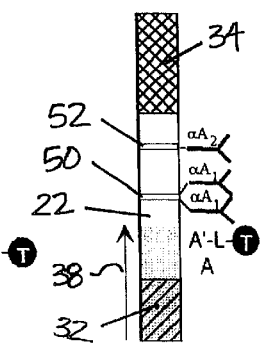
Figure 1E:
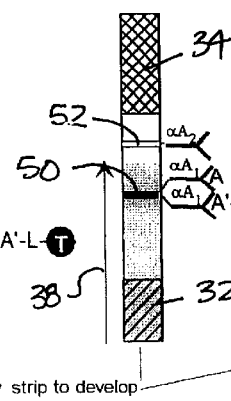
Figure 1F:
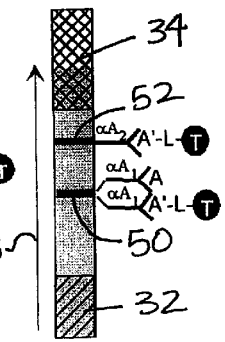

Capture agents (such as specific binding partners, for example antibodies such as monoclonal antibodies) are aligned in spaced indicator lines 50, 52, each of which extends transversely on the strip. A mobilization zone 54 is located on collection member 22 between pad 30 and indicator line 50. The mobilization zone 54 contains an analyte (or analyte analog) linked to a tag, hereinafter referred to as an A-L-T conjugate. In the embodiment illustrated in FIG. 1, the analyte-tracer conjugate is dried in mobilization zone 54 on strip 20. In this embodiment, the fluid sample, applied to sample pad 30 (FIG. 1C) and moves through pad 30 and overlapping extension 32. The sample then migrates by capillary action through the porous material of collection member 22 (FIG. 1D). As the fluid sample migrates through the porous material, it mobilizes the analyte-tracer conjugate A-L-T, which then flows with the liquid sample through the primary capture line 50 (FIG. 1E) and secondary capture line 52 (FIG. 1F), into reservoir 34. As shown in FIGS. 1E and 1F, the presence of analyte in the sample is detected by a positive signal (a color change) in secondary capture line 52.

The illustrated embodiment incorporates different monoclonal antibodies in each indicator line, and the monoclonal antibodies of the primary and secondary capture zones have different affinities for the analyte and conjugate. In a specifically illustrated embodiment, the primary monoclonal antibodies of the primary capture zone are all the same, and have an equal or greater affinity for the analyte than the conjugate. The monoclonal antibodies are attached to the substrate in a known fashion, and binding of conjugate to these antibodies provides is detectable (such as by a change in color, electrical conductivity, fluorescence, or magnetic polarity) if the labeled conjugate binds to the capture agent. The secondary capture area serves as the readout area, indicating the test result. The test results can be visualized directly, or may be measured using a reader device (e.g., a scanner). Such reader devices may detect color or fluorescence from the readout area.

The sample pad 30 may be a pad of polyester, glass fiber, or cellulose, to which the fluid sample is applied. The collection member 22 may, for example, be a porous material such as nitrocellulose. The reservoir pad 34, for absorbing excess fluid that flows through the collection member 22, is composed for example of cellulose or any fluid-absorbent material. The backing support 28 may be a plastic such as polyvinylchloride (PVC) or any other liquid-impervious material. The antibodies or binding partners that are immobilized in the primary and secondary capture lines 50, 52 may be the same or different, and the antibodies or binding partners in each capture area may be immobilized in single or multiple (distinct) lines (although only a single line 50 and single line 52 are shown in FIG. 1). Primary capture line 50 can also serve as a control area to indicate that the device is functioning properly, since the presence of signal from primary capture line 50 indicates that the conjugate is present, and that the capture agent binds the conjugate.

Embodiment of FIG. 2

A-L-T Conjugate Mobilization Zone Under Sample Pad

Another embodiment of a lateral flow chromatography strip 120 is seen in isolation in FIGS. 2A and 2B, which is similar to FIGS. 1A and 1B, and wherein like parts have been given like reference numbers plus 100. FIGS. 2A and 2B show strip 120 to include an elongated, narrow, bibulous liquid collection member 122 with a flat proximal edge 124 and a flat distal edge 126. Strip 120 is mounted on a rigid or semi-rigid plastic support 128, and a proximal absorbent sample collection pad 130 is also mounted to the support 128 such that it is contiguous with collection member 122, and includes a reduced thickness extension 132 that extends in a distal direction over member 122. A distal reservoir pad 134 is attached to a distal end of support 128, and reservoir pad 134 includes a reduced thickness extension 136 that overlaps subjacent collection member 122. Liquid placed on collection pad 130 moves by capillary action in a distal direction 138 through collection member 122 into reservoir pad 134.

Capture agents (such as specific binding partners, for example antibodies such as monoclonal antibodies) are aligned in spaced indicator lines 150, 152, each of which extends transversely on the strip, and respectively form the primary and secondary capture zones. A mobilization zone 154 is located on collection member 122 underneath pad 130 and indicator line 150. The mobilization zone 154 contains an analyte (or analyte analog) linked to a tag (and referred to as an A-L-T conjugate). In the embodiment illustrated in FIG. 2, the analyte-tracer conjugate is dried in mobilization zone 154 on strip 120 prior to pad 132 being applied to support 128. In this embodiment, the fluid sample is applied to sample pad 130 (FIG. 2C), which mobilizes the A-L-T conjugate in mobilization zone 154. The A-L-T conjugate moves with the liquid sample through pad 130 and overlapping extension 132 (FIG. 2D). The A-L-T conjugate can also be dried in mobilization zone 154 on pad 132 before pad 132 is applied to support 128.

Since the sample is applied to the surface of pad 130, it is believed that it encounters less resistance and migrates more quickly through pad 130 than the subjacent A-L-T conjugate (which must be hydrated and mobilized), and it is believed that the sample (and any analyte in the sample) therefore reaches the primary capture line 150 (FIG. 2E) before the A-L-T conjugate. Once the A-L-T conjugate reaches the antibodies in primary capture line 150, the specific binding sites are already occupied by any analyte from the sample, which reduces the number of binding sites available to bind A-L-T. Hence the A-L-T conjugate continues to migrate by capillary action through the porous material of collection member 122 until it reaches secondary capture line 152 (FIG. 2F), where it is bound by the specific binding partner immobilized therein. As shown in FIGS. 2E and 2F, the presence of analyte in the sample is detected by a positive signal (a color change) in secondary capture line 152.

The illustrated embodiment incorporates different monoclonal antibodies in each indicator line, and the monoclonal antibodies of the primary and secondary capture zones have the same or different affinities for the analyte and conjugate. In a specifically illustrated embodiment, the primary monoclonal antibodies of the primary capture zone are all the same, and the secondary monoclonal antibodies of the secondary capture zone are all the same. However, the primary monoclonal antibodies have an equal or greater affinity for the analyte than the conjugate. In the embodiment in which the primary antibody has a greater affinity for the analyte than the conjugate, the primary antibodies preferentially bind the analyte, which further inhibits binding of the A-L-T conjugate in primary capture line 150. The unbound A-L-T therefore more readily moves through primary capture line 150 to bind at secondary capture line 152.

As with the embodiment of FIG. 1, the secondary capture line 152 provides an indication (such as a change in color, electrical conductivity, fluorescence, or magnetic polarity) if the labeled A-L-T conjugate binds to the capture agent.

Embodiment of FIG. 3

Separate Introduction of A-L-T Conjugate on to Strip

Figure 3A:
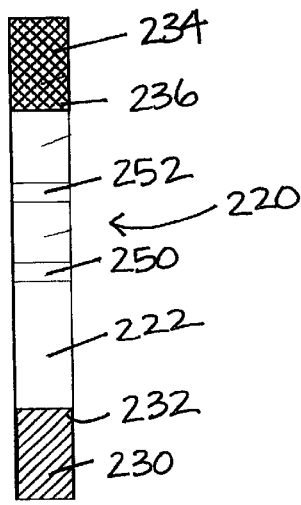
FIG. 3A is a top plan view of a third embodiment of the test strip.
Figure 3B:
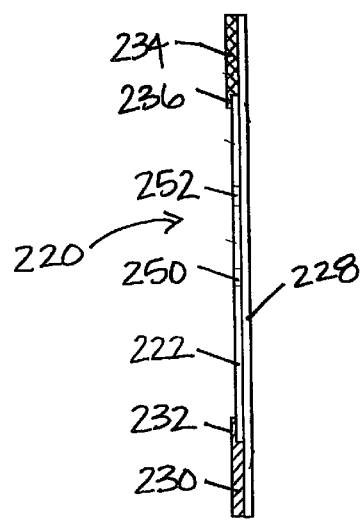
FIG. 3B is a side view of the test strip shown in FIG. 3A

A third embodiment of a lateral flow chromatography strip 220 is seen in FIGS. 3A and 3B, which is similar to FIGS. 1A and 1B, and wherein like parts have been given like reference numbers plus 200. In this embodiment, the A-L-T conjugate is not present on the strip itself, but is instead applied separately to strip 220 after the sample has been placed on the strip, so that the sample (and any analyte contained therein) will reach the primary and secondary capture lines 250, 252 before the A-L-T conjugate.

FIGS. 3A and 3B show strip 220 to include an elongated, narrow, bibulous liquid collection member 222 with a flat proximal edge 224 and a flat distal edge 226. Strip 220 is mounted on a rigid or semi-rigid plastic support 228, and a proximal absorbent sample collection pad 230 is also mounted to the support 228 such that it is contiguous with collection member 222, and includes a reduced thickness extension 232 that extends in a distal direction over member 222. A distal reservoir pad 234 is attached to a distal end of support 228, and reservoir pad 234 includes a reduced thickness extension 236 that overlaps subjacent collection member 222. Liquid placed on collection pad 230 moves by capillary action in a distal direction 238 through collection member 222 into reservoir pad 234.

Figure 3C:
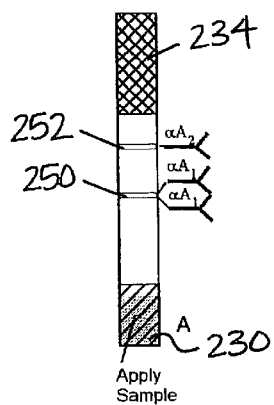
FIGS. 3C–3F are schematic tops views of the test strip of FIG. 3A, illustrating the progressive advancement of a liquid specimen through the strip.
Figure 3D:
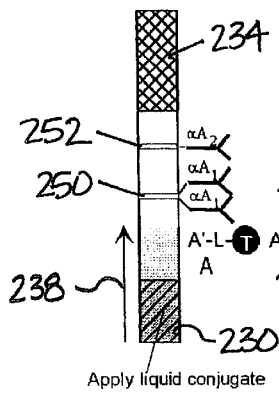
Figures 3E, 3F:
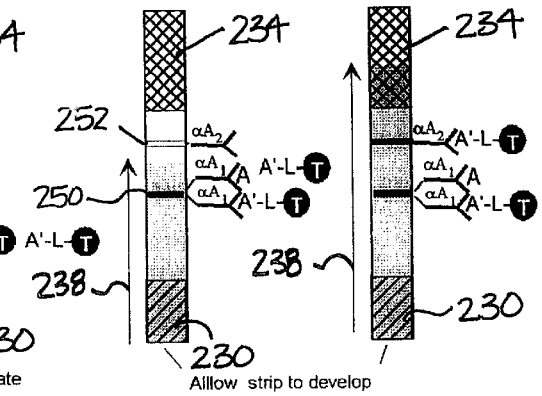

In this third embodiment, the A-L-T conjugate is applied in liquid form to the sample application pad 230 (FIG. 3D) during or soon after application of the sample to pad 230 (FIG. 3C). If the A-L-T conjugate is applied after application of the sample to pad 230, and at substantially the same place on pad 230, then the sample will reach capture lines 250, 252 prior to the A-L-T conjugate reaching the capture lines. Alternatively, the sample and A-L-T conjugate may be applied substantially simultaneously to pad 230 (not shown), but the sample is applied at a more distal position on strip 220 (closer to primary capture line 250). The sample and analyte-tracer conjugate then migrate at substantially a same rate by capillary action through the porous material of strip 220. However, the sample (and any analyte therein) reaches primary capture line 250 before the A-L-T conjugate, such that any analyte binds to the specific capture agents in primary capture line 250, and occupies binding sites that are unavailable for binding of the A-L-T conjugate to capture line 250. Hence the unbound A-L-T conjugate continues to migrate through the strip to secondary capture line 252, where it is bound and provides a signal of its presence (which correlates to the presence and amount of analyte in the test sample).

If analyte is not present in the sample, binding of A-L-T conjugate occurs at primary capture line 250, and all (or substantially all) of the A-L-T conjugate is bound at primary line 250, so that a signal is absent or weak at secondary line 252. Moreover, since the signal at secondary line 252 is proportional to the quantity of A-L-T conjugate that is not bound by primary line 250, and which migrates to secondary line 252, the intensity of the signal from secondary line 252 is proportional to a concentration of analyte in the sample.

In another embodiment, the sample and A-L-T conjugate can be designed to migrate at different rates through the porous strip, to allow any analyte in the sample to reach the primary capture line before the A-L-T conjugate. For example, the A-L-T conjugate can be a very large molecule that migrates more slowly than the free analyte in the sample. For example, a bovine serum albumin is a very large molecule that can be used as a linker L between the analyte analog A and tracer T, which can increase the size and molecular weight of the A-L-T conjugate relative to the free analyte. Hence, the smaller free analyte will migrate more quickly through the strip than the large A-L-T conjugate. For instance, the tracer molecule can be selected (based on size, polarity, charge, or other such characteristics) to provide specific migration characteristics.

By way of example only, colloidal gold particles can be as small as about 20 nm, but may be larger. In specific examples wherein colloidal gold particles are used as the tracer element of an A-L-T of this invention, the particles will be about 30 nm, about 40 nm, about 50 nm, or about 60 nm or larger, depending in part on the migration characteristics desired. Likewise, in embodiments that incorporate latex particles (e.g., colored latex particles) as the tracer element, latex particles can be about 200 nm, about 250 nm, about 300 nm, about 350 nm, or about 400 nm or larger. However, when large tracer elements are used, it is important that the diameter of the entire A-L-T complex be taken into account. It is possible that, if the diameter of the entire complex is greater than the typical pore size of the porous flow material, the complex (or a portion thereof) may be trapped and not migrate. In addition, large A-L-T complexes might in some instances create steric hindrance that reduces the interaction between the analyte or analyte analog and the immobilized binding partner. In each instance, however, with the provision of the methods herein, empirical testing of individual, specific A-L-T complexes, as well as combinations of A-L-T and the particular immobilized binding partner(s) and porous flow material(s), is enabled.

In these three illustrated embodiments, the fluid migrates along the porous material of the strip by capillary action into the reservoir pad. Once the reservoir pad becomes saturated, the fluid migration automatically stops.

In these three illustrated embodiments, the specific analyte and analyte-tracer conjugate particles sequentially "compete" for binding to the specific binding partner localized at the primary capture area, in that the analyte (if any is present) first contacts the binding partner in the primary area and the conjugate (which follows after) can only bind to specific binding partners that remain unoccupied. In the case where a sample does not contain the specific analyte, the analyte-tracer conjugate particles bind with the binding partner in the primary capture zone. Minimal or no analyte-tracer particle is then available for travel to and binding with the immobilized binding partner in the secondary capture area, resulting in no signal. In the case where a sample contains the specific analyte to be detected, the binding partner in the primary capture area binds free analyte in the sample and there are fewer (if any) primary capture binding sites available for binding to the analyte-tracer complex. The portion of analyte-tracer complex that fails to bind to binding sites in the first capture area (due to previous binding by the analyte) will be captured by the immobilized binding partner in the secondary capture "read-out" area. As applied sample contains increasing amounts of target analyte, greater amounts of analyte-tracer particles (unbound in the primary capture area) are free to bind to the secondary capture area, resulting in an increased signal.

III. Positive Detection Lateral Flow Devices and Methods

Devices according to the invention generally include a strip of absorbent material, which can be made of different substances each joined to the other in zones, which may be abutted and/or overlapped. The absorbent strips are fixed on a solid support. Zones within each strip may differentially contain the specific binding partner(s) and/or other reagents required for the detection and/or quantification of the particular analyte being tested for. Thus these zones can be viewed as functional sectors or functional regions within the test device. In general, a fluid sample (or a sample suspended in a fluid) is introduced to the strip at the proximal end of the strip, for instance by dipping or spotting. The fluid migrates distally through all the functional regions of the strip. The final distribution of the fluid in the individual functional regions depends on the adsorptive capacity and the dimensions of the materials used. Within these bounds, substantial variation exists within the several examples of the devices of this invention, as will be explained below.

The described methods and devices can be used to detect any small or large analyte having at least one binding-specific epitope that permits the binding of a specific binding partner. This invention relies on the binding of one binding partner to a single epitope on the analyte, rather than the binding of two binding partners (each of which binds to a different epitope on the analyte) as in used in classic "sandwich" format immunochromatographic tests; therefore the disclosed methods and devices can detect analytes smaller than about 1,000 Daltons. Such small analytes generally do not have two epitopes, and thus cannot be detected using a sandwich format assay.

A. Construction and Configuration

In some embodiments, the sample application pad (such as pad 32 in FIGS. 1A and 1B) can have the function of a volume-metering element, as described in German Patent Nos. 3,043,608 and 2,332,760, and U.S. Pat. Nos. 3,464,560, 3,600,306, 3,667,607, 3,902,847, 4,144,306 and 4,258,001. Examples of the sample application pad are a piece of fabric or paper which is located at one end of the test element and which becomes completely saturated with a volume (for instance, a definite or measured volume) of liquid merely by being dipped into a fluid, for example a solution of the sample, and then releases the liquid to the succeeding zones more slowly and in a controlled manner. The pad has dimensions such that it takes up sufficient fluid to permit the fluid to migrate to the other end of the device, to the reservoir pad or absorption zone (such as pad 34 in FIGS. 1A and 1B). The absorption pad has the function of absorbing excess and freely mobile reagent components and reaction products of the signal-producing system.

The absorbent materials that form the strip of the disclosed devices can, for instance, be composed of cellulose;

chemical derivatives of cellulose or of plastics having a porous or fibrous structure and adequately hydrophilic properties; particles such as cellulose or silica gel embedded in a synthetic membrane; and also of natural products that are hydrophilic but have been rendered insoluble in water. A combination of strips composed of different materials can be used. Suitable absorbent materials are selected on the basis of the requirements set for the particular assay device. Nitrocellulose, commonly used to bind and immobilize proteins and polyethylene glycols, is one example of a material for use in making the collection member of the test strips of this invention. Polysulfones, nylons or other porous membranes capable of adsorbing macromolecules also provide examples of strip material for use with devices and methods of this invention.

The liquid impervious backing, to which the sample application pad, porous (absorbent) material strip(s), and reservoir pad are attached, may be polyvinylchloride (PVC) or any other liquid-impervious material.

Test strips of the invention will usually be arranged linearly, with the sample application zone (area) being at the proximal end of the strip, and the reservoir pad (adsorption zone) being at the distal end of the strip. Between these two ends will be located the primary and secondary capture zones, with the primary capture zone located closer to the application zone and the secondary capture zone located closer to the reservoir pad. The mobilizable analyte-tracer conjugate (A-L-T) can be located beneath the application zone (covered by the sample pad), or distal to the application zone (e.g., between the application zone and the primary capture zone). Mobile analyte-tracer conjugate (which is added to the test strip at the same time as or after application of the sample) can be placed at any point along the test strip so long as it is proximal to the primary capture zone.

Individual components of the devices of this invention are arranged in such a way that the sample suspected of containing analyte contacts the primary (first) capture zone before the analyte tracer conjugate does. This permits the analyte (if present) to bind to the available binding sites first, followed by the binding of analyte-tracer conjugate to any remaining vacant specific binding sites in the first capture area. The delay in the analyte-tracer conjugate contact with the first capture area can be achieved by the arrangement of the analyte-tracer conjugate on the test strip (for instance by placing the analyte-tracer conjugate distal to the sample application area), by adding the analyte-tracer conjugate to the test strip at the same time or after application of the sample, or by providing delayed-release reversible immobilization of the analyte-tracer conjugate to the surface of the test device strip. Such delayed-release can be accomplished, for example, through application of the A-L-T complex to the test strip material in the presence of one or more co-molecules, such as sucrose (about 5–50%), mannitol (about 5–30%); glycerol (about 1–15%), PVA (about 0.1–5%), PVP (about 0.1–5%), or mixtures thereof.

Certain embodiments of the current invention will include at least one filter element, which is placed at the sample application zone or between the sample application zone and the primary capture line. Such a filter element may increase the sensitivity of the assay by removing unwanted components in the fluid sample and yet allowing unimpeded passage of labeled analyte. Thus, a proportionately greater amount of analyte binds to the assay read-out area, and more accurate assay results are achieved.

B. Choice of Analyte

The assay device of this invention can detect small analytes, for instance those of interest in medical diagnostics. Small analytes can, for instance, be nutrients, peptides, hormones (e.g., human chorionic gonadotropin (hCG), frequently assayed as a marker of human pregnancy, estrogen or progesterone), drugs (both therapeutic drugs such as antibiotics, tranquilizers and anticonvulsants, and drugs of abuse such as cocaine, heroin, and marijuana), environmental pollutants (e.g., pesticides and aromatic hydrocarbons), and vitamins, as well as derivatives, metabolites (catabolites or anabolites), fragments or analogs of these molecules. One specific example of a small analyte is cotinine, a major metabolite of nicotine, detection of which can be used for determining the smoking status of an individual.

Larger analytes detectable using the methods and devices disclosed herein can be antigens (for instance, antigens specific to bacterial, viral, and protozoan pathogens, such as Streptococcus, hepatitis virus, and Giardia), antibodies (such as antibodies induced as a result of infection with pathogens, such as antibodies to the bacterium *Helicobacter pylori* and to human immunodeficiency virus), enzymes (such as aspartate aminotransferase, lactate dehydrogenase, alkaline phosphatase, glutamate dehydrogenase, and other indicators of physiological function and/or tissue damage), and other proteins (such as hemoglobin, frequently assayed in determinations of fecal occult blood, an early indicator of gastrointestinal disorders such as colon cancer).

C. Choice of Binding Partner(s)

The binding partner(s) (e.g., antibodies) immobilized on the porous material of the test device may be applied directly or through a carrier molecule such as protein A, protein G, or anti-immunoglobulin. One common technique used to immobilize protein-derived binding partners (e.g., antibodies) onto nitrocellulose or another solid support is to irreversibly adsorb them onto the solid support. Methods for attaching the binding partner(s) to such carrier molecules are well known, and can for instance involve the use of one or more linking groups.

The diagnostic devices and methods described in the present invention can be used in any binding pair reactions, for instance those reactions having immunochemical components such as antibodies, antigens, and haptens. In those assays in which the detection of analyte molecules is described herein, the molecules immobilized in the assay indicator zones are analyte binding molecules. In some examples, both immobilized reagents will be anti-analyte antibodies. The antibodies can be either monoclonal or polyclonal, the methods of producing which are well known in the art. Any combination of monoclonal-polyclonal antibodies can be employed.

The immobilized specific binding partner in the primary capture zone will have an affinity for the analyte being tested for, and an affinity for the analyte-tracer conjugate being used as a reporting molecule. When the first binding partner does not have a lower binding affinity (has an equal or greater binding affinity) for the analyte-tracer conjugate than it has for the analyte, the analyte-tracer conjugate is at least as likely to bind to the immobilized binding partner in the first binding zone as will a molecule of the analyte being tested for. In some embodiments, the first binding partner will have a higher affinity for the analyte-tracer than it has for the analyte, but it will have at least some affinity for the analyte. The absolute values of these binding affinities, however, are not essential to the invention; rather, it is the relative affinity of the analyte and the analyte-tracer conjugate for the first immobilized specific binding partner that is important. A lower or equal affinity for the analyte-tracer conjugate helps increase the likelihood that this molecule, traversing the first capture area after the analyte has done so, does not dislodge a significant amount of the analyte from the immobilized binding partner molecules.

The secondary capture zone can also contain one or more distinct lines of immobilized antibody or binding partner. This second immobilized binding partner can but need not be the same as the immobilized binding partner in the first binding zone. In embodiments where the first and second immobilized binding partners are different, the second binding partner may have a high binding affinity for the analyte-tracer complex and will have the same, less or no binding affinity to free analyte that is being measured. In particular embodiments, this second immobilized binding partner will not have a higher binding affinity for the analyte than it does for the analyte-tracer conjugate.

The purpose of the second capture area is to trap the analyte-tracer conjugate that was not trapped in the first capture area, thereby generating a signal that can be read as the result of the test.

D. Choice of Ligand/Analog/Analyte-Tracer Conjugate

The invention includes the use of an analyte-tracer conjugate. The analyte-tracer conjugate includes an analyte or analyte-analog, such that the conjugate shares or mimics at least one three-dimensional determinant(s) of the native analyte to be detected. In sharing at least one binding determinant with the analyte target, the analyte-tracer conjugate can bind to at least certain specific binding partners that bind the analyte. The analyte tracer conjugate also includes some sort of reporter molecule, for example a visible colored or fluorescent particle such as a polystyrene latex microsphere, or colloidal gold. The tracer can be attached to the analyte (or analyte analog) by a linking group. Other examples of reporter (tracer) molecule are an enzyme, fluorophore, or other molecule known to produce a detectable and/or measurable product or signal.

The analyte-tracer conjugate generally includes at least one label that makes the amount of the bound analog detectable and/or recordable by measuring techniques. Labels can be, for example: radioactive isotopes, enzymes, fluorescent, phosphorescent or luminescent substances, substances having stable unpaired electrons, erythrocytes, latex particles (including dyed latex such as described in WO 88/08534, EP-A 0 280 559 and 0 281 327), magnetic particles, metal sols (such as gold sol particles such as those described in U.S. Pat. No. 4,313,734), dye sol particles such as described in U.S. Pat. No. 4,373,932 and WO 88/08534, and dyes encapsulated in liposomes, as described in U.S. Pat. No. 4,703,017.

In some examples, the analyte analog (analyte-tracer conjugate) will be bound to or otherwise associated with another, non-labeling molecule. This carrier molecule can function, for instance, to attach the label (tracer) to the analyte analog (as discussed above), and/or may provide additional stability or longevity to the analyte-tracer conjugate. Examples of such carrier molecules are bovine serum albumin (BSA), polyethylene glycol (PEG) (the use of which is described in hereby incorporated U.S. Pat. No. 6,033,918), avidin or streptavidin, and immunoglobulins.

E. Choice and Preparation of Sample

The choice of the sample will in part be governed by the analyte to be detected. It will be obvious that the sample should be chosen to be one in which it is suspected the analyte may be present. Medically relevant substances (e.g., analytes) can be found in blood (including antibodies, antigens, drugs, hormones, enzymes, metabolites, peptides and so forth), tears, sweat, and other secretions and exudates.

For instance, many substances (e.g., analytes) of medical significance can be found in saliva (Malamud and Tabak (eds.), *Saliva as a Diagnostic Fluid, Ann. NY Acad. Sci.,* 1993, ISBN #08 976 67883). These include drugs (e.g., illegal or abused drugs such as marijuana or alcohol, as described in U.S. Pat. No. 5,968,746), drug metabolites (such as cotinine, a bi-product of nicotine metabolism), hormones (such as estriol, which is linked to risk of pre-term labor (McGregor et al., *Am. J. Obstet. Gynecol.,* 173:1337–1342, 1995)), electrolytes (such as those useful in monitoring ovulation, as described in U.S. Pat. No. 5,914,271), antibiotics, infectious agents (e.g., through the presence of antibodies to the infectious agents, as described for instance in U.S. Pat. No. 5,942,403), and so forth.

The use of saliva samples for medical tests is now well known, as are methods for the collection, preparation (such as filtration or pretreatment of the sample, see below), and preservation (see for instance U.S. Pat. No. 5,968,746) of saliva samples. Saliva can be collected using, for instance, a sponge, an absorbent pad, a salt-impregnated absorbent pad, chewable substrates, an aspirator (e.g., a straw, capillary tube, or syringe), a mouth rinse, or by expectoration. Specialized devices or mechanisms also can be used to collect saliva samples (see, e.g., U.S. Pat. Nos. 6,022,326 and 5,871,905). Certain devices for collection of oral fluids are commercially available, for instance, from Epitope, Inc., Beaverton, Oreg., or Saliva Diagnostic Systems, Vancouver, Wash.

It will be beneficial with certain samples to remove at least a portion of any particulates that may be in the sample. Such particulates (depending on the sample) may include blood cells, other cellular debris, food or other oral particles, and/or sediment (e.g., from natural water samples). Such particulates can be removed using techniques that are well known, including filtration and sedimentation.

As disclosed in U.S. Pat. No. 5,871,905, adding mixtures of bile salts (or their corresponding acid forms) and, optionally, agents which chelate or sequester divalent ions to saliva or other oral samples may reduce the incidence of false positives sometimes seen with such samples. For examples of the disclosed devices and methods, the bile acid or salt (such as deoxycholic acid (deoxycholate salt), cholic acid (cholate salt), chenodeoxycholic acid (chenodeoxycholate salt), glycodeoxycholic acid (glycodeoxycholate salt), and/or taurodeoxycholic acid (taurodeoxycholate salt)) is present in a concentration sufficient to reduce the rate of occurrence of false positives in the assay. Examples of chelators include, but are not limited to, EDTA, EGTA, NTA, CDTA, sodium citrate, and a chelating resin. For instance, EDTA concentrations in the final sample used in the assay can range from about 0.005 M to about 0.05 M.

IV. Kits for Detection and/or Quantification of Analyte

Assay devices according to the invention can be provided in the form of kits. Such kits will include one or more assay devices (which may be for the same or different analytes), and instructions for the use of the device(s). The instructions may provide direction on how to apply sample to the test device, how to apply analyte-tracer conjugate in those kits wherein the device does not have conjugate dried thereon, the amount of time necessary or advisable to wait for results to develop, and details on how to read and interpret the results of the test. Such instructions may also include standards, such as standard tables, graphs, or pictures for comparison of the results of a test. These standards may optionally include the information necessary to quantify analyte using the test device, such as a standard curve relating intensity of signal or number of signal lines to an amount of analyte therefore present in the sample.

19

In those embodiments wherein the analyte-tracer conjugate is added to the test device after or during application of the sample, the kit will also include an aliquot of the analyte-tracer analog. Such aliquot can be provided in solubilized or solubilizable form, and will be provided in a container. In certain kits, the amount of analyte-tracer conjugate provided will be sufficient for use with a single assay device, where as other kits (particularly those which contain more than one assay device) will contain sufficient analyte-tracer compound to perform several tests.

EXAMPLES

The following examples are provided to illustrate certain particular features of the present invention. These examples should not be construed to limit the invention to the particular features described.

Example 1

Cotinine Test with Liquid Analyte Tracer Conjugate

Reagents

A bovine serum albumin (BSA)-cotinine conjugate was prepared using cotinine trans-4-carboxylic acid as follows: To 0.25 ml of a mixture of dimethylformamide and pyridine (1/1 by volume) was added 5 mg of trans-4-carboxycotinine (Sigma-Aldrich, St. Louis, Mo.), 5 mg of N-hydroxysuccinimide and 15 mg of 1-ethyl-3-(3-dimethylaminopropyl) carbodiimide hydrochloride (Sigma-Aldrich, St. Louis, Mo.). The mixture was rotated to dissolve, and then left rotating for 1 h to form the active ester as described previously (Fjrowell and Landon, *Ann. Clin. Biochem.* 23: 596–602, 1986). A 50 µl aliquot of this active ester was added to 1 ml of 10 mg/ml of BSA solution in 0.1 M phosphate buffer (pH 7.4). The reaction mixture was rotated at room temperature for 4 hours, then dialyzed against 10 mM phosphate buffer (pH 7.4). The BSA-cotinine conjugate was diluted to a concentration of 5 mg/ml bovine serum albumin in 10 mM phosphate buffer (pH 7.4) and stored.

The BSA-cotinine conjugate was coupled to carboxyl blue latex particles using 1-ethyl-3-(3-dimethylaminopropyl) carbodiimide to form the cotinine-tracer conjugate as follows: To 1.0 ml of 10 mg/ml of carboxyl latex particles (0.33 µm, Bangs Laboratories, Fishers Ind.) in 0.1 M phosphate buffer (pH 7.0) was added 10 mg of 1-ethyl-3-(3-dimethylaminopropyl) carbodiimide. The mixture was shaken for 20 minutes at room temperature. The activated latex particles were centrifuged and then suspended in 1 ml of 1 mg/ml of BSA-cotinine conjugate (5 mg/ml BSA-cotinine conjugate diluted 1:5 in 0.1 M borate buffer, pH 8.0). The reaction mixture was rotated at room temperature for 3 hours. To this reaction mixture was added 10 µl of 10% BSA (in distilled water) to block the unreacted sites. The resulting cotinine-tracer conjugate was washed twice with 10 mM phosphate buffer (pH 7.4) containing 0.1% BSA, 1 mM EDTA and 0.05% Tween 20. The cotinine-tracer conjugate was suspended to a concentration of 10 mg/ml latex in the same phosphate buffer and stored.

Anti-cotinine antibody (MAb1) was purified from tissue culture medium by protein A agarose chromatography (see Example 6, below).

Anti-cotinine-BSA antibody (MAb2) was purified from tissue culture medium by protein A agarose chromatography (see Example 6, below).

Goat-anti mouse IgG (GAM) antibody was purified from serum by affinity chromatography using standard techniques.

20

Cotinine (Sigma-Aldrich, St. Louis, Mo.) test solutions (10, 50, 100 and 200 ng/ml) were prepared in a saliva matrix (75 mM phosphate buffered saline, pH 7.4, 2.5 mM EDTA, 0.05% Triton X100, 0.05% IGEPAL, 0.1% sodium benzoate, 0.1% potassium sorbate, 6 mM potassium chloride, 10 mM potassium carbonate, 6 mM sodium chloride, 5 mM sodium phosphate, 0.1 mM magnesium chloride, 1 mM calcium chloride, and 50 µg/ml BSA, 500 µg/ml mucin).

Construction of Test Strips

A 2.4×30 cm strip of nitrocellulose was affixed to a 15 mil adhesive coated vinyl backing.

MAb1 was mixed (1:1) with GAM to form a stable soluble complex. One line of a 1.0 mg/ml solution of the MAb1-GAM complex was applied to (sprayed on) the nitrocellulose membrane (capture/control line) to produce a total applied complex of 1 µg/linear centimeter. One line of a 500 µg/ml solution of MAb2 was applied to (sprayed on) the nitrocellulose membrane (test/read line) to produce a total applied complex of 0.5 µg/linear centimeter. The nitrocellulose membrane was dried for 10 minutes at 37° C., then blocked with a stabilized buffer (StabilGuard™, Surmodics Inc., Eden Prairie, Minn.) diluted with an equal volume of 150 mM phosphate buffered saline (pH 7.4, 0.05% sodium azide), and dried again for 30 minutes at 37° C.

A polyester pad was wetted by immersion in a 1.0% Triton X-100 solution in 100 mM phosphate buffer at pH 7.4, then laminated onto the lower portion of the strip to act as a sample wick. A cellulose pad was laminated to the upper portion of the strip to act as absorbent reservoir.

The completed card was cut into 4 mm strips. Strips were inserted into plastic housings with a hole/well located in the sample application area and a window in the test reading area.

Test Procedure

A 20 µl aliquot of cotinine test solution was added to the sample well of each test strip device and allowed to absorb for 10–30 seconds. Thereafter, 20 µl of cotinine-tracer conjugate was added to the sample well of each test strip device. The test strips were allowed to develop for 5–10 minutes.

Results

Figure 4:
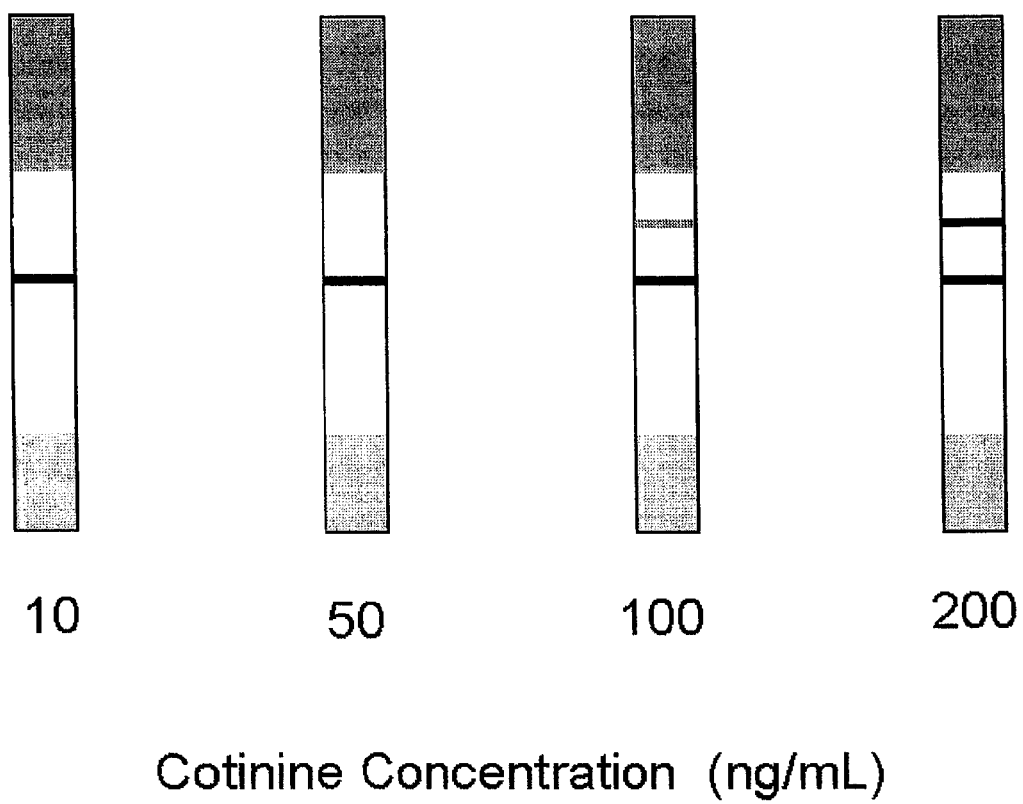
FIG. 4 is a schematic view of a series of test strips to which have been applied different concentrations of an analyte, which illustrates how quantitative information about the concentration of the analyte can be obtained from the intensity of test bands shown on the strip.

The test strips were read visually. The results are depicted in FIG. 4 and summarized below:

10 ng cotinine/ml: control line visible, no test line visible;
50 ng cotinine/ml: control line visible, weak test line visible;
100 ng cotinine/ml: control line visible, strong test line visible; and
200 ng cotinine/ml: control line visible, very strong test line visible.

Figure 5:
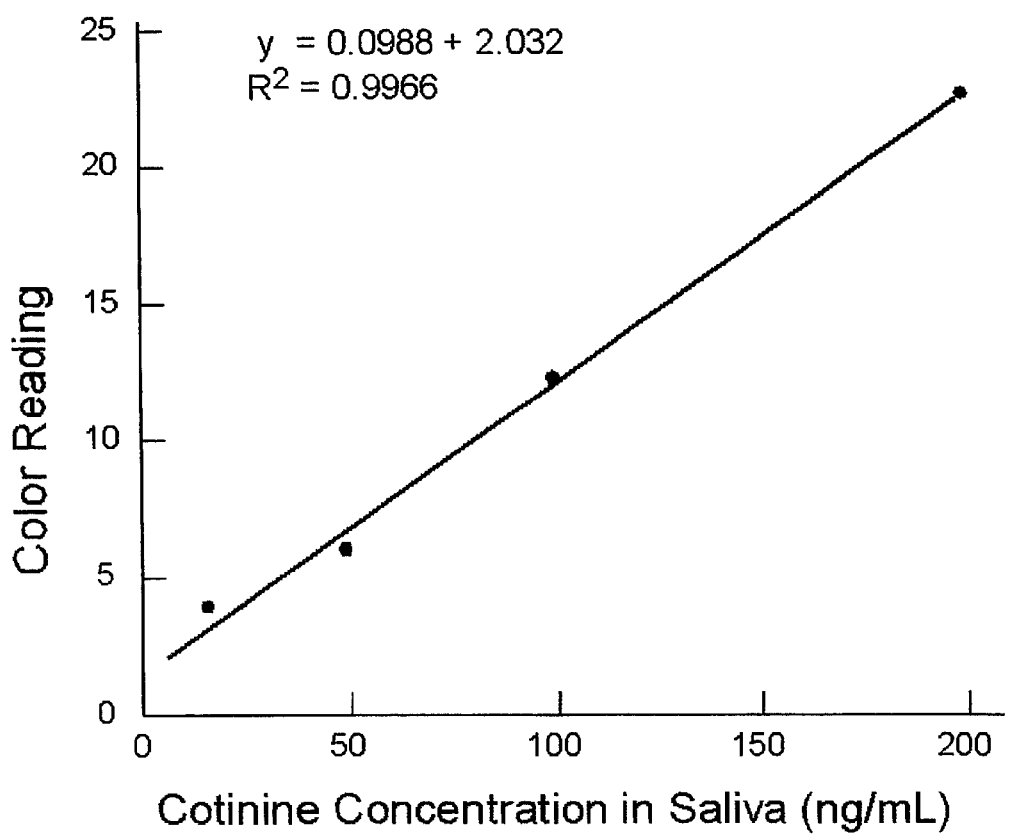
FIG. 5 is a graph that illustrates a substantially linear relationship between a color reaction on the test strip and a cotinine analyte concentration in a saliva test specimen.

The color intensity of the test line on each test strip was read with a Minolta CR241 calorimeter. The direct relationship between the color intensity reading and cotinine concentration in the saliva matrix is summarized in FIG. 5.

Example 2

Cotinine Test With Multiple Read Lines

Reagents

A BSA-cotinine conjugate prepared as in Example 1 was coupled to carboxyl blue latex particles using 1-ethyl-3-(3-dimethylaminopropyl) carbodiimide as described in Example 1.

Anti-cotinine monoclonal antibody (MAb1) as described in Example 1 was diluted to 1 mg/ml in PBS (pH 7.4, 0.5% azide).

Goat-anti mouse IgG antibody (GAM) was purified from serum by affinity chromatography using standard techniques.

Cotinine (Sigma-Aldrich, St. Louis, Mo.) test solutions (0, 20, 200, 500 ng/ml) were prepared in saliva matrix as described above.

Test Strips

A 2.4×30 cm strip of nitrocellulose was affixed to a 15 mil adhesive coated vinyl backing. MAb1 solution was mixed with GAM to form a stable soluble MAb-GAM complex. One line of a 1.0 mg/ml MAb1-GAM complex was applied to (sprayed on) the nitrocellulose membrane (capture/control zone) to produce a total applied complex of 1 µg/linear centimeter.

Four lines of a 220 µg/ml solution of the MAb1-GAM complex were applied to (sprayed on) the nitrocellulose membrane (test/read zone) to produce a total applied complex of 22 ng/linear centimeter. The membrane was dried for 10 minutes at 37° C., then blocked with a stabilized buffer as described in Example 1, and dried again for 30 minutes at 37° C.

A polyester pad, pretreated with surfactant as described in Example 1, was laminated onto the lower portion of the strip to act as a sample wick. A cellulose pad was laminated to the upper portion of the strip to act as absorbent reservoir.

The completed card was cut into approximately 4 mm strips. Strips were inserted into plastic housings with a hole/well located in the sample application area and a window in the test reading area.

Test Procedure

A 20 µl aliquot of cotinine test solution was added to the sample well of each test strip device and allowed to absorb to the membrane for 10–30 seconds. Thereafter, 20 µl of cotinine-tracer conjugate was added to the sample well of each test strip device. The test strips were allowed to develop for 10–15 minutes, then read visually.

Results

Figure 6:
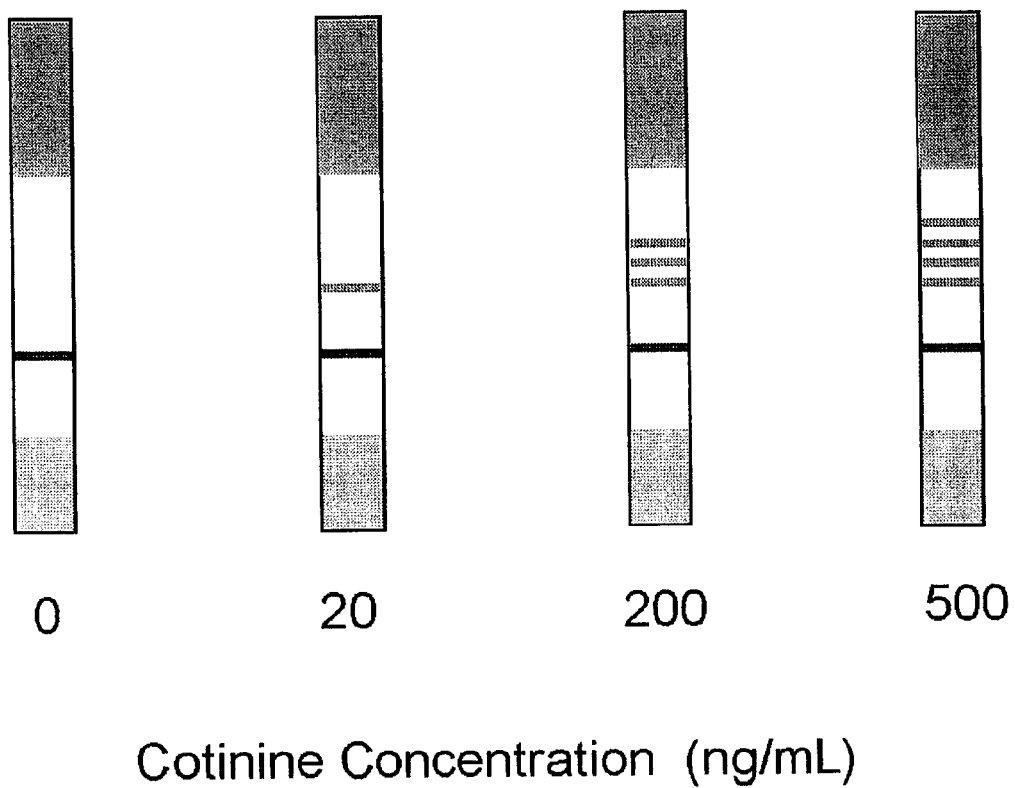
FIG. 6 is a schematic view similar to FIG. 4, but showing a strip with four indicator lines, which quantitatively indicate an amount of analyte in the sample.

The results are exemplified in FIG. 6 and summarized below:

0 ng cotinine/ml: control line visible, no test line visible;
20 ng cotinine/ml: control line visible, one test line visible;
200 ng cotinine/ml: control line visible, three test lines visible; and
500 ng cotinine/ml: control line visible, four test lines visible.

Example 3

Cotinine Test with Analyte-Tracer Conjugate on the Glass-Fiber Pad

Reagents

Cotinine-tracer conjugate, goat-anti mouse IgG antibody (GAM), anti-cotinine antibody (MAb1) and cotinine test solutions were prepared as described in Example 2.

Construction of Test Strips

A 25.4 mm×300 mm strip of nitrocellulose was affixed to a 15 mil adhesive coated vinyl backing, to provide support. The cotinine antibody (MAb 1) was mixed 1:1 with goat-anti mouse IgG (GAM) to form stable soluble complexes at a final concentration of 1 mg/ml. Two lines of the MAb1-GAM complex were applied to the nitrocellulose membrane; a total of 1 µg/linear centimeter was applied to each line. The membrane was dried for 15 minutes at 37° C.

Cotinine-tracer conjugate was diluted to 1.5 mg/ml with a conjugate buffer containing 10 mm Phosphate pH 7.4, 0.1% BSA, 0.05% Tween, 10 mm EDTA, 0.1% sodium azide and 20% sucrose. Four lines of the diluted cotinine-tracer conjugate solution were applied 1 mm apart to the glass fiber pad (approximately 21 cm from the bottom of the strip) at 1.5 µg/linear centimeter for each line. The application of the four lines was repeated and the pad dried for 1 hour at 37° C. in a drying oven.

The dried glass fiber pad was laminated onto the lower portion of the strip to act as a sample wick. An untreated cellulose pad was laminated to the upper portion of the strip to act as an absorbent reservoir.

The completed assay strips were cut to 4 mm in width and stored in a sealed foil pouch with approximately 1 gram of clay desiccant until used.

Test Procedure

Three test strips were removed from the foil pouch and placed on a flat surface. A 100 µl test sample (containing 0, 20 or 200 ng cotinine/mi buffer) was applied to the sample application zone of each test strip. The strips were allowed to develop for 20 minutes and were then read visually.

Results

The visual reading results are summarized below:

0 ng cotinine/ml: strong control line visible, no test line visible;
20 ng cotinine/ml: strong control line visible, weak test line visible; and
200 ng cotinine/ml: strong control line visible, strong test line with intensity equal to the control line.

Example 4

Cotinine Test with Analyte-Tracer Conjugate on the Nitrocellulose

Reagents

Cotinine-tracer conjugate was prepared as described in Example 2. Goat-anti mouse IgG antibody (GAM), anti-cotinine antibody (MAb1) and cotinine test solutions were prepared as described in Example 2.

Test Strips

The cotinine antibody (MAb1)/goat-anti mouse IgG antibody (GAM) solution was applied to a strip of vinyl-backed nitrocellulose and dried as described in Example 3. Cotinine-tracer conjugate was diluted with a conjugate buffer as described in Example 3. The tracer conjugate was diluted to 750 µg/ml and applied to the nitrocellulose membrane at 0.75 µg/linear centimeter. A total of four lines were applied 1 mm apart, beginning at the base (approximately 26 mm from the bottom of the strip). The strip was dried for 1 hour at 37° C. in a drying oven.

An untreated cellulose pad was laminated to the upper portion of the strip to act as an absorbent reservoir. A 26 mm×300 mm strip of "Accuflow G" glass fiber material (Schleicher and Schuell, Inc., Keene N.H.) for use as a sample pad was placed overlapping the top conjugate line to facilitate slow release of the cotinine-tracer conjugate.

The prepared test strips were cut to 4 mm widths and stored in a sealed foil pouch with approximately 1 gram of clay desiccant until used.

Test Procedure

Test strips were removed from the foil pouch and placed on a flat surface. A 90 μl test sample (containing 0, 20 or 200 ng cotinine/ml buffer) was applied to the sample application zone of each test strip. The strips were allowed to develop for 20 minutes and then read visually.

Results

The strip with the sample pad overlapping the highest cotinine-tracer conjugate line gave the following visual results:

0 ng cotinine/ml: strong control line, no test line;

20 ng cotinine/ml: strong control line, detectable test line; and 200 ng cotinine/ml: strong control line, strong test line with intensity equal to the control line.

Example 5

Methamphetamine Test With Analyte-Tracer Conjugate on the Nitrocellulose

Reagents

A methamphetamine-tracer conjugate was prepared methods similar to those described in Example 1 using methamphetamine-BSA conjugate (Arista Biological, Inc., Bethlehem, Pa.) instead of BSA-cotinine. Goat-anti mouse IgG antibody (GAM) was also obtained from Arista Biologicals. Methamphetamine monoclonal antibody was obtained from Omega Biological, Inc (Bozeman, Mont.; Cat. #100-11-183, Clone Met 2). Methampetamine HCl (Sigma-Aldrich, St. Louis, Mo.) was used to prepare test solutions of 0, 10, and 100 ng/ml in saliva matrix (as described in Example 1).

Test Strips

One line of a 1.0 mg/ml solution of methamphetamine antibody/goat-anti mouse IgG antibody (GAM) complex was applied to a strip of vinyl-backed nitrocellulose membrane (capture/control line) to produce a total applied complex of 1 μg/linear centimeter. Likewise, one line of a 1.0 mg/ml solution of methamphetamine antibody/goat-anti mouse IgG antibody (GAM) complex was applied to a strip of vinyl-backed nitrocellulose membrane (test/read line) to produce a total applied complex of 1 μg/linear centimeter. The strip was then dried as described in example 1.

Methamphetamine-tracer conjugate was diluted to 750 μg/ml with a conjugate buffer as described in Example 3, then applied to the nitrocellulose membrane at 0.75 μg/linear centimeter. A total of four lines were applied 1 mm apart, beginning at the base (approximately 26 mm from the bottom of the strip). The strip was dried for 1 hour at 37° C. in a drying oven.

An untreated cellulose pad was laminated to the upper portion of the strip to act as an absorbent reservoir. A 26 mm×300 mm strip of "Accuflow G" glass fiber material, for use as a sample pad, was placed overlapping the top conjugate line to facilitate slow release of the methamphetamine-tracer conjugate.

The prepared test strips were cut to 4 mm widths and stored in a sealed foil pouch with 1 gram of clay desiccant until used.

Test Procedure

Test strips were removed from the foil pouch and placed on a flat surface. A 90 μl aliquot of a test sample (0, 10, 100 ng methamphetamine HCl/ml buffer) was applied to the sample application zone of each test strip. The strips were allowed to develop for 20 minutes and then read visually.

Results

The strips gave the following visual results:

0 ng methamphetamine HCl/ml: strong control line, no test line;

10 ng methamphetamine HCl/ml: strong control line, detectable test line; and 100 ng methamphetamine HCl/ml: strong control line, strong test line with intensity equal to the control line Example 6

Preparation of Antibodies

Immunogen Preparation

A bovine serum albumin (BSA)-cotinine conjugate was prepared using cotinine trans-4-carboxylic acid as follows: To 0.25 ml of a mixture of dimethylformamide and pyridine (1/1 by volume) was added 5 mg of trans-4-carboxycotinine (Sigma-Aldrich, St. Louis, Mo.), 5 mg of N-hydroxysuccinimide and 15 mg of 1-ethyl-3-(3-dimethylaminopropyl) carbodiimide hydrochloride (Sigma-Aldrich, St. Louis, Mo.). The mixture was rotated to dissolve, and then left rotating for one hour to form the active ester as described previously (Fjrowell and Landon, *Ann Clin Biochem*, 23:596–602, 1986). A 50 μl aliquot of this active ester was added to 1 ml of a 10 mg/ml BSA solution in 0.1 M phosphate buffer (pH 7.4). The reaction mixture was rotated at room temperature for four hours, then dialyzed against 10 mM phosphate buffer (pH 7.4).

The BSA-cotinine conjugate was diluted to a concentration of 5 mg/ml bovine serum albumin in 10 mM phosphate buffer (pH 7.4). The BSA-cotinine conjugate was stored aseptically in sterile 10 mM phosphate buffer (pH 7.4) at 4° C. One (1.0) mg of this material was supplied for immunizations. In addition, 1.0 mg of free cotinine (Sigma-Aldrich, product #C 5923) was supplied for booster immunizations.

Immunization Protocol

Four Balb/c female mice, age five weeks, were immunized using the following procedure. Immunogen (BSA-cotinine, as prepared above) at 1 mg/ml was mixed with an equal volume of RIBI adjuvant (Corixa, Seattle, Wash.). Each mouse received 20 μg total protein per subcutaneous injection on days 0, 7 and 21. Retro-orbital collection of blood was performed on day 35. Serum from each mouse was extracted by centrifuging at 3000×g for ten minutes, and titers of each serum were measured using a sandwich ELISA method. After resting for ~30 days, the mouse with the strongest anti-cotinine titer was boosted with an intraperitoneal injection of the BSA-cotinine conjugate (50 μg prepared in RIBI adjuvant) and an intravenous injection of free cotinine (5 μg in 0.1 M phosphate buffered saline, pH 7.4). Fusion of splenocytes from the mouse to NSO cells (Balb/c myeloma, non-secreting) was performed four days after the boost. Mother clones (polyclonals) were initially screened using the ELISA method described below. Positive mother clones were further sub-cloned. Monoclones were isolated using limiting dilution.

Antibody Selection

An initial screen was performed using sandwich ELISA. High-binding 96-well microtiter plates (Nalge Nunc, Rocherster, N.Y.) were coated overnight at 4° C. with 1 µg/well of BSA-cotinine diluted in 10 mM phosphate buffered (pH 7.4) saline (PBS). The coating solution was removed by inversion of the plate. Cell supernatant (100 µl) was added to each well and incubated for one hour at 37° C. The plate was washed five times with PBS containing 0.05% Tween 20. Goat anti-mouse heavy and light chain antibody (GAM) conjugated to horseradish peroxidase (HRP) (Jackson ImmunoResearch Labs, West Grove, Pa.) was diluted 1:5000 in PBS-Tween. A 100 µl aliquot of the diluted HRP preparation was added to each well and incubated for 30 minutes at 37° C. Positive wells were visualized by adding 100 µl of One-step TMB substrate (Kirkegaard & Perry Laboratories, Gaithersburg, Md.) to each well, followed by incubation for 15 minutes at room temperature. A second ELISA screen (for specificity) was performed on initial positives using BSA-coated wells. The final ELISA assay was performed using wells coated with two-fold dilutions of immunogen from 100 ng/well to 1 ng/well, keeping antibody concentration constant.

All ELISA assays used cell supernatants from cultures at mid-growth phase, and at 1:5 or 1:10 dilutions. Approximately 10 ml of supernatant from each of the highest titered clones was stored at −20° C. for later testing.

Selection of the anti-cotinine clones for differential affinities was performed using a lateral flow immunochromatographic assay. Immunochromatographic test strips were prepared as described in Example 1. The primary capture zone consisting of two transversely oriented lines of goat anti-mouse (GAM-IgG) IgG antibody (1 µg/µl in PBS) applied beginning approximately 3 mm from the origin of the nitrocellulose. The two lines were placed 1 mm apart to produce a total applied complex of 1 µg/linear centimeter. The secondary capture zone consisted of one line of streptavidin (2 mg/ml) applied approximately 5 mm from the second line of the primary capture zone to produce a total applied complex of 0.5 µg/linear centimeter.

After application of the primary and secondary capture molecules, the strips were allowed to dry, then blocked by immersion in a blocking buffer (0.5% BSA, 4% sucrose 150 mM phosphate buffered saline, pH 7.4) for one minute, to prevent further protein adsorption. The strips were then dried for ten minutes at 37° C.

Latex-BSA-cotinine-biotin conjugate was prepared as described in Example 1 (above).

The tissue culture supernatants were tested as follows:
1) 25 µl of each supernatant was added to separate 12×75 mm borosilicate glass test tubes;
2) either 125 µl of a solution of free cotinine (250 ng/ml) in a buffer (10 mM phosphate buffered saline, 0.05% Tween 20, 0.1% BSA, pH 7.4) or 125 µl of buffer without cotinine, was added to each tube;
3) 1.5 µl of latex-BSA-cotinine-biotin (10 mg/ml) was added to each tube; and
4) one test strip was added to each tube and allowed to run to completion (approximately 12 minutes).

The optimum clone for the primary antibody showed two distinct and important characteristics:
1) In the tubes containing buffer alone (no free cotinine), 100% binding of the conjugate in the GAM-IgG primary capture zone, with the highest percentage of conjugate bound by the first line within that zone; and
2) In the tubes containing the 25 ng of free cotinine, displacement of a relatively high percentage of latex conjugate, measured by binding in the secondary capture zone.

These binding characteristics are indicative of a similar affinity of the clone for both free and bound cotinine.

The optimum clone for the secondary capture zone exhibited only binding in the primary capture zone, with the highest percentage bound by the first line within that zone, and did not exhibit any displacement by free cotinine. This type of binding characteristic indicates that the clone has an affinity for only the bound form of cotinine.

The optimum clone for primary capture was clone #5-3H, and the optimum clone for secondary capture was clone #10-3A.

Antibody Production & Purification

Once optimum clones were selected, the appropriate cell lines were frozen and stored in liquid nitrogen. Growth of the hybridoma cell lines was initiated from frozen cells in 24-well tissue culture plates in a hybridoma growth medium consisting of DMEM (high glucose)/10% FetalClone® 1 serum (HyClone, Logan, Utah). Cells were maintained at 2 to 7×100,000 cells/ml by expansion into fresh medium twice weekly. A CELLine™CL 1000 (Integra Biosciences, Jamesville, Md.) was used for antibody production (see manufacturers instructions) with up to $10^9$ cells in less than 12 ml of hybridoma growth medium in the inner chamber. The outer chamber contained 950 ml of serum-free DMEM. Approximately ⅓ to ⅔ of outer chamber was collected twice weekly, followed by volume replacement with fresh medium.

Purification of the monoclonal antibodies was achieved directly from the growth medium over a column with recombinant Protein A immobilized on porous glass beads (ProSep A; Pierce Chemical Co., Rockford, Ill.), following the manufacturers instructions. Immediately following purification, the monoclonal antibodies were dialyzed against one liter of 10 mM phosphate buffered saline (0.05% sodium azide, pH 7.4) in Spectra/Por® 7, 10,000 MW cut-off membrane (Spectrum Laboratories, Rancho Dominguez, Calif.) for 24 hours with at least two buffer changes.

In view of the many possible embodiments to which the principles of our invention may be applied, it should be recognized that the illustrated embodiments are only examples of the invention and should not be taken as limitations on the scope of the invention. Rather, the scope of the invention is defined by the following claims. We therefore claim as our invention all that comes within the scope and spirit of these claims.

We claim:

1. A method for detecting and/or quantitating an analyte in a liquid sample, comprising:
   (a) providing a test strip comprising
      a mobilization zone;
      a mobile or mobilizable detectable tracer in the mobilization zone;
      a sample application area;
      a primary capture area comprising a first immobilized binding partner having a binding affinity for the analyte and a binding affinity for the detectable tracer; and a secondary capture area comprising a second immobilized binding partner having a binding affinity for the detectable tracer;

wherein the sample application area, mobilization zone, primary capture area and secondary capture area are in a path of liquid flow from the sample application area distally through the mobilization zone to the primary capture area and then to the secondary capture area, wherein a distal flow of analyte reaches the primary capture area before a distal flow of tracer reaches the primary capture area;

(b) contacting the liquid sample with the sample application area of the test strip, and allowing the liquid sample to mobilize the detectable tracer such that the detectable tracer migrates with the liquid sample, wherein the detectable tracer has a weight greater than the analyte to permit analyte flow to move at a faster rate than the tracer flow along the path of liquid flow, such that the tracer flow reaches the primary capture zone after analyte flow in the liquid sample reaches the primary capture area;

wherein the analyte flow that reaches the primary capture zone occupies first immobilized binding partner such that subsequent binding of detectable tracer to first immobilized binding partner is inhibited, whereby unbound detectable tracer continues along the path of liquid flow distally to bind to second immobilized binding partner and provide a signal from the secondary capture area that indicates the presence of the analyte in the liquid sample.

2. A test strip for determining presence and/or amount of an analyte in a liquid sample comprising:

a mobilization zone;

a mobile or mobilizable detectable tracer in the mobilization zone;

a sample application area;

a primary capture area comprising a first immobilized binding partner having a binding affinity for the analyte and a binding affinity for the detectable tracer; and a secondary capture area comprising a second immobilized binding partner having a binding affinity for the detectable tracer;

wherein the sample application area, mobilization zone, primary capture area and secondary capture area are in a path of liquid flow from the sample application area through the mobilization zone to the primary capture area and then to the secondary capture area, wherein the detectable tracer has a weight greater than a weight of the analyte such that a tracer flow migrates more slowly than an analyte flow along the path of liquid flow, whereby the analyte flow reaches the primary capture area before the tracer flow reaches the primary capture area.

3. The test strip of claim 1, further comprising at least one filter pad in the path of liquid flow.

4. The test strip of claim 3, wherein the filter pad is pretreated with at least one reagent to enhance the sensitivity of the assay device.

5. The test strip of claim 4, wherein the at least one reagent is selected from the group consisting of buffers, detergents, and anticoagulants.

6. The test strip of claim 1, wherein the first and second immobilized binding partners are antibodies, antigens, haptens, lectins or receptors.

7. The test strip of claim 1, wherein the first and second immobilized binding partners for the analyte are identical.

8. The test strip of claim 1, wherein the first and second immobilized binding partners are each anti-analyte antibodies.

9. The test strip of claim 1, wherein the detectable tracer comprises an analyte analog.

10. The test strip of claim 1, wherein the detectable tracer comprises a visually detectable label.

11. The test strip of claim 1, wherein the detectable tracer comprises a detectable tracer for an analyte selected from the group consisting of an antigen of an infectious disease, an antigen to an antibody of an infectious disease, a hormone, a growth factor, a therapeutic drug, a drug of abuse, a product of the metabolism of a drug of abuse, and a hapten.

12. The test strip of claim 11, wherein the detectable tracer comprises a detectable tracer for an analyte comprising an antibody selected from the group consisting of an antibody to Human Immunodeficiency Virus (HIV), an antibody to Human T-Cell Lymphotropic Virus (HTLV), an antibody to *Helicobacter pylori*, an antibody to hepatitis, an antibody to measles, an antibody to mumps, and an antibody to rubella.

13. The test strip of claim 11, wherein the detectable tracer comprises a detectable tracer for an analyte comprising a therapeutic drug or drug of abuse or products of the metabolism of a drug of abuse, wherein the analyte is selected from the group consisting of tetrahydrocannabinol, nicotine, cotinine, ethanol, theophylline, phenytoin, acetaminophen, lithium, diazepam, nortryptyline, secobarbital, and phenobarbitol, methamphetamine and fragments, mimetics, analogs or derivatives thereof.

14. The test strip of claim 13, wherein the detectable tracer comprises a detectable tracer conjugate for an analyte that is a product of metabolism of a drug of abuse, and the product of metabolism comprises cotinine.

15. The test strip of claim 11, wherein the detectable tracer comprises a detectable tracer conjugate for an analyte comprising a hormone, and the hormone is selected from the group consisting of testosterone, estradiol, estriol, 17-hydroxyprogesterone, progesterone, thyroxine, thyroid stimulating hormone, follicle stimulating hormone, and luteinizing hormone, and fragments, mimetics, analogs or derivatives thereof.

16. The test strip of claim 1, wherein a quantity of the second specific binding partner in the secondary capture area is such that the quantity of detectable tracer binding to the secondary capture area, and by correlation the amount of the analyte in the liquid sample, is indicated by an intensity of a detection signal of the detectable tracer in the secondary capture area.

17. The test strip of claim 1, wherein the secondary binding area of the test strip is divided into at least two discrete and non-overlapping bands, with a quantity of the second specific binding partner in each band being such that quantity of tracer binding to the secondary capture area, and by correlation the amount of the analyte in a tested sample, is indicated by a number of bands to which the tracer molecule binds.

18. The method of claim 1, further comprising quantifying an amount of analyte in the liquid sample, wherein the amount of analyte in the liquid sample determines an intensity of the signal from the tracer in the secondary capture area.

19. The method of claim 1, wherein the liquid sample migrates along the test strip in the path of liquid flow by capillary action.

20. The method of claim 1, wherein the analyte has a molecular weight of about 100–1,000 Daltons.

21. The method of claim 1, wherein the analyte has a molecular weight of greater than 1,000 Daltons.

22. The method of claim 1, wherein the detectable tracer comprises an analyte or analyte analog linked to a detectable molecule by a linker.

23. The method of claim 22, wherein the linker is selected to increase the weight of the detectable tracer.

24. The method of claim 23, wherein the linker comprises bovine serum albumin (BSA).

25. The test strip of claim 2, further comprising at least one filter pad in the path of liquid flow.

26. The test strip of claim 25, wherein the filter pad is pretreated with at least one reagent to enhance the sensitivity of the assay device.

27. The test strip of claim 26, wherein the at least one reagent is selected from the group consisting of buffers, detergents, and anticoagulants.

28. The test strip of claim 2, wherein the first and second immobilized binding partners are antibodies, antigens, lectins, receptors or haptens.

29. The test strip of claim 2, wherein the first and second immobilized binding partner for the analyte are identical.

30. The test strip of claim 2, wherein the first and second immobilized binding partner are each anti-analyte antibodies.

31. The test strip of claim 2, wherein the detectable tracer is a tracer conjugate comprising an analyte or an analyte analog.

32. The test strip of claim 2, wherein the detectable tracer comprises a visually detectable label.

33. The test strip of claim 2, wherein the detectable tracer comprises a detectable tracer for an analyte selected from the group consisting of an antigen of an infectious disease, an antigen to an antibody of an infectious disease, a hormone, a growth factor, a therapeutic drug, a drug of abuse, a product of the metabolism of a drug of abuse, and a hapten.

34. The test strip of claim 2, wherein the detectable tracer comprises a detectable tracer for an analyte comprising an antibody selected from the group consisting of an antibody to Human Immunodeficiency Virus (HIV), an antibody to Human T-Cell Lymphotropic Virus (HTLV), an antibody to *Helicobacter pylori*, an antibody to hepatitis, an antibody to measles, an antibody to mumps, and an antibody to rubella.

35. The test strip of claim 2, wherein the detectable tracer comprises a detectable tracer for an analyte comprising a therapeutic drug or drug of abuse or products of the metabolism of a drug of abuse, wherein the analyte is selected from the group consisting of tetrahydrocannabinol, nicotine, cotinine, ethanol, theophylline, phenytoin, acetaminophen, lithium, diazepam, nortryptyline, secobarbital, and phenobarbitol, methamphetamine and fragments, mimetics, analogs or derivatives thereof.

36. The test strip of claim 2, wherein the detectable tracer comprises a detectable tracer for an analyte that is a product of metabolism of a drug of abuse, and the product of metabolism comprises cotinine.

37. The test strip of claim 33, wherein the detectable tracer comprises a detectable tracer for an analyte comprising a hormone, and the hormone is selected from the group consisting of testosterone, estradiol, estriol, 17-hydroxyprogesterone, progesterone, thyroxine, thyroid stimulating hormone, follicle stimulating hormone, and luteinizing hormone, and fragments, mimetics, analogs or derivatives thereof.

38. The test strip of claim 2, wherein a quantity of the second specific binding partner in the secondary capture area is such that the quantity of detectable tracer binding to the secondary capture area, and by correlation the amount of the analyte in the liquid sample, is indicated by an intensity of a detection signal of the detectable tracer in the secondary capture area.

39. The test strip of claim 2, wherein the secondary binding area of the test strip is divided into at least two discrete and non-overlapping bands, with a quantity of the second specific binding partner in each band being such that quantity of tracer binding to the secondary capture area, and by correlation the amount of the analyte in a tested sample, is indicated by a number of bands to which the tracer molecule binds.

* * * * *

UNITED STATES PATENT AND TRADEMARK OFFICE
CERTIFICATE OF CORRECTION

PATENT NO.        : 6,699,722 B2
APPLICATION NO.   : 09/835304
DATED             : March 2, 2004
INVENTOR(S)       : Bauer et al.

It is certified that error appears in the above-identified patent and that said Letters Patent is hereby corrected as shown below:

Column 5, line 14, "FIG. 3A" should be --FIG. 3A.--.

Column 5, line 45, "pO" should be deleted.

Column 8, line 1, "includes" should be --include--.

Column 8, line 33, "analyte, analog" should be --analyte-analog--.

Column 10, line 33, "sample, applied" should be --sample is applied--.

Column 10, line 52-53, "provides" should be deleted.

Column 14, line 41, "as in" should be --as is--.

Column 17, line 31, "molecule" should be --molecules--.

Column 21, line 14, "MAb-GAM" should be --MAb1-GAM--.

Column 21, line 30, "as absorbent" should be --as an absorbent--.

Column 22, line 1, "(MAb 1)" should be --(MAb1)--.

Column 22, line 28, "/mi" should be --/ml--.

Column 23, line 33-34, "prepared methods" should be --prepared using methods--.

Column 25, line 11, "Rocherster" should be --Rochester--.

Column 26, line 32, "manufacturers" should be --manufacturer's--.

Column 26, line 42, "manufacturers" should be --manufacturer's--.

In Claim 3 (Col. 27, line 55), "test strip" should be --method--.

In Claim 4 (Col. 27, line 57), "test strip" should be --method--.

In Claim 5 (Col. 27, line 60), "test strip" should be --method--.

In Claim 6 (Col. 27, line 63), "test strip" should be --method--.

UNITED STATES PATENT AND TRADEMARK OFFICE
CERTIFICATE OF CORRECTION

PATENT NO. : 6,699,722 B2
APPLICATION NO. : 09/835304
DATED : March 2, 2004
INVENTOR(S) : Bauer et al.

It is certified that error appears in the above-identified patent and that said Letters Patent is hereby corrected as shown below:

In Claim 7 (Col. 27, line 66), "test strip" should be --method--.

In Claim 8 (Col. 28, line 1), "test strip" should be --method--.

In Claim 9 (Col. 28, line 4), "test strip" should be --method--.

In Claim 10 (Col. 28, line 6), "test strip" should be --method--.

In Claim 11 (Col. 28, line 8), "test strip" should be --method--.

In Claim 12 (Col. 28, line 15), "test strip" should be --method--.

In Claim 13 (Col. 28, line 22), "test strip" should be --method--.

In Claim 14 (Col. 28, line 31), "test strip" should be --method--.

In Claim 15 (Col. 28, line 35), "test strip" should be --method--.

In Claim 16 (Col. 28, line 43), "test strip" should be --method--.

In Claim 17 (Col. 28, line 50), "test strip" should be --method--.

Signed and Sealed this

Sixth Day of November, 2007

JON W. DUDAS
*Director of the United States Patent and Trademark Office*